(12) United States Patent
Scott

(10) Patent No.: US 6,669,725 B2
(45) Date of Patent: Dec. 30, 2003

(54) ANNULOPLASTY RING FOR REGENERATION OF DISEASED OR DAMAGED HEART VALVE ANNULUS

(75) Inventor: Timothy L. Scott, Sugar Land, TX (US)

(73) Assignee: Centerpulse Biologics Inc., Houston, TX (US)

( * ) Notice: Subject to any disclaimer, the term of this patent is extended or adjusted under 35 U.S.C. 154(b) by 0 days.

(21) Appl. No.: 09/750,588

(22) Filed: Dec. 28, 2000

(65) Prior Publication Data

US 2002/0123803 A1 Sep. 5, 2002

(51) Int. Cl.[7] .................................................. A61F 2/24
(52) U.S. Cl. ..................................... 623/2.36; 623/2.42
(58) Field of Search ................................ 623/2.36, 2.37

(56) References Cited

U.S. PATENT DOCUMENTS

| | | | |
|---|---|---|---|
| 3,656,185 A | 4/1972 | Carpentier | 3/1 |
| 5,061,277 A | 10/1991 | Carpentier et al. | 623/2 |
| 5,290,763 A | 3/1994 | Poser et al. | 514/21 |
| 5,306,296 A | 4/1994 | Wright et al. | 623/2 |
| 5,371,191 A | 12/1994 | Poser et al. | 530/350 |
| 5,376,112 A | 12/1994 | Duran | 623/2 |
| 5,563,124 A | 10/1996 | Damien et al. | 514/21 |
| 5,674,279 A | 10/1997 | Wright et al. | 623/2 |
| 5,728,152 A | 3/1998 | Mirsch, II et al. | 623/2 |
| 5,855,610 A | 1/1999 | Vacanti et al. | 623/11 |
| 5,895,420 A | 4/1999 | Mirsch, II et al. | 623/2 |
| 6,024,918 A | 2/2000 | Hendriks et al. | 422/44 |
| 6,102,945 A | 8/2000 | Campbell | 623/2.37 |
| 6,113,636 A | 9/2000 | Ogle | 623/11.11 |
| 6,143,024 A | 11/2000 | Campbell et al. | 623/2.36 |
| 6,143,354 A | 11/2000 | Koulik et al. | 427/2.24 |
| 6,211,157 B1 | 4/2001 | Benedict et al. | 514/21 |
| 6,375,680 B1 * | 4/2002 | Carlyle | 623/11.11 |
| 6,416,548 B2 * | 7/2002 | Chinn et al. | 623/2.36 |

FOREIGN PATENT DOCUMENTS

WO   WO 97/16135   5/1997

* cited by examiner

Primary Examiner—David H. Willse
Assistant Examiner—Javier G. Blanco
(74) Attorney, Agent, or Firm—Timothy L. Scott; Kenneth S. Barrow; Christopher R. Kirby

(57) ABSTRACT

An improved, non-resorbable annuloplasty ring that will provide support for the valve annulus while also promoting healing and/or regeneration of the annulus tissue is disclosed. Healing and/or regeneration of valvular tissue is promoted using a growth factor mixture that has been shown to be capable of promoting growth of a wide range of tissues, including heart valve tissue, and which promotes tissue growth based upon the local tissue environment (i.e., specific cell recruitment and proliferation). Thus, an annuloplasty ring that provides an actual healing response in addition to mechanical support to a dilated heart valve annulus is provided.

13 Claims, 36 Drawing Sheets

FIGURE 2
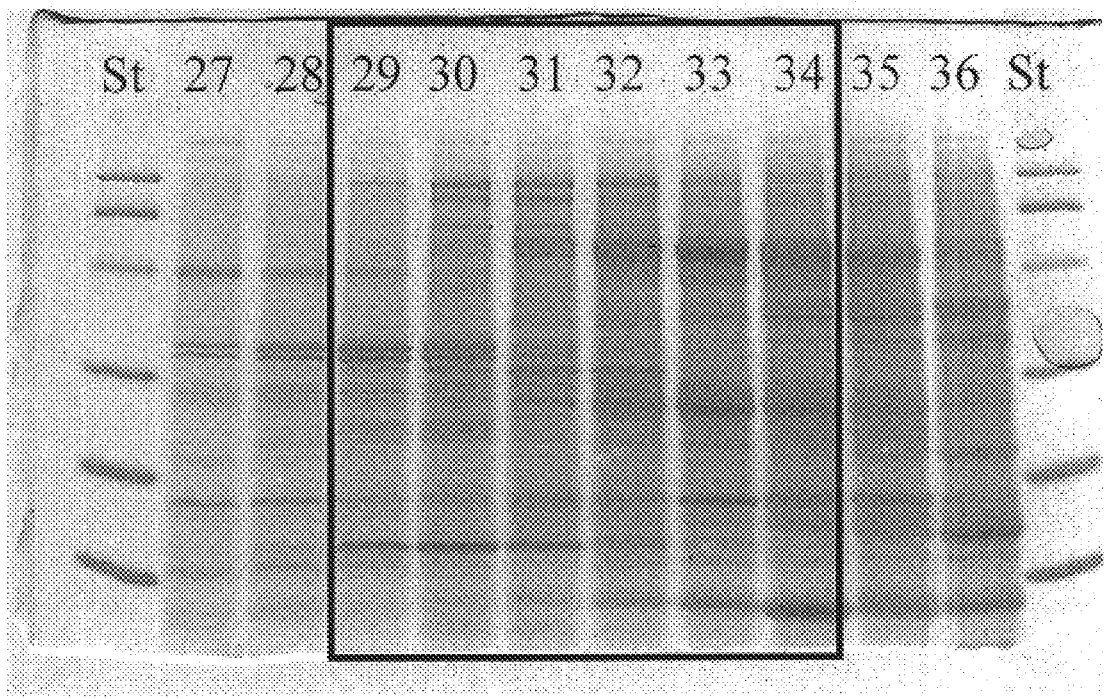
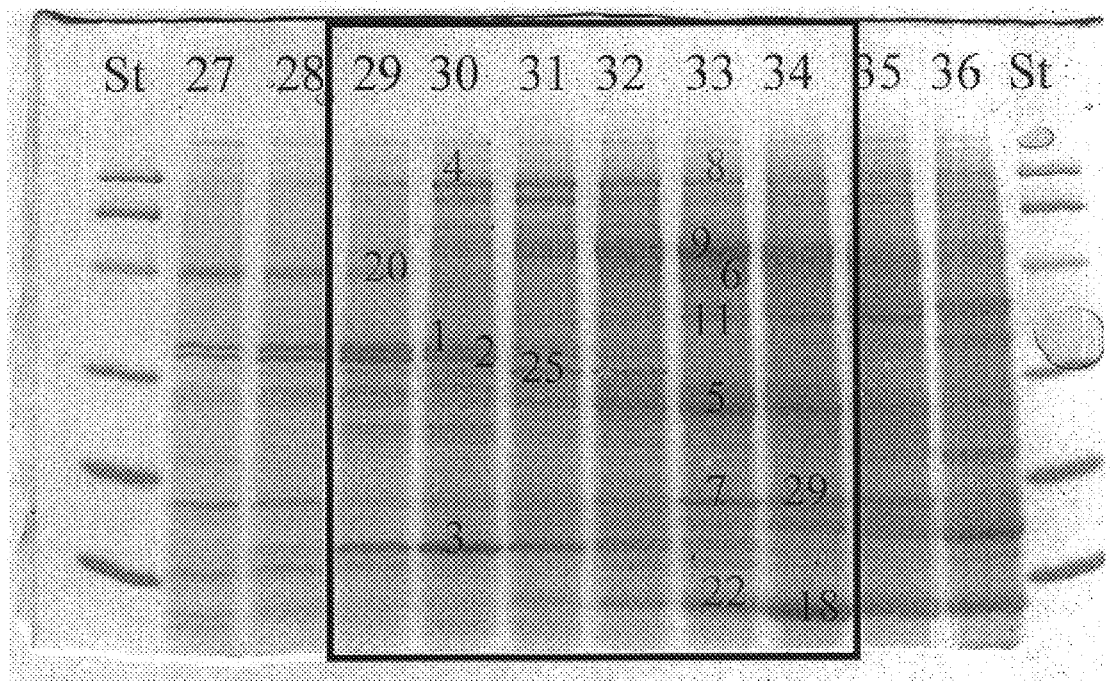
FIGURE 3

| Band No. | Identity |
|---|---|
| 1 | Histone H1.c |
| 2 | Histone H1.c |
| 3 | Ribosomal protein RS20 |
| 4 | Similar to ribosomal protein LORP |
| 5 | BMP-3 |
| 6 | α2 macroglobulin RAP and BMP-3 |
| 7 | Similar to ribosomal protein LORP |
| 8 | BMP-3 |
| 9 | BMP-3 |
| 11 | Ribosomal protein RL6 and BMP-3 |
| 18 | TGF-β2 / SPP 24 |
| 20 | Factor H |
| 22 | TGF-β2 |
| 25 | BMP-3 and H1.x |
| 29 | BMP-3 and ribosomal protein RL32 |

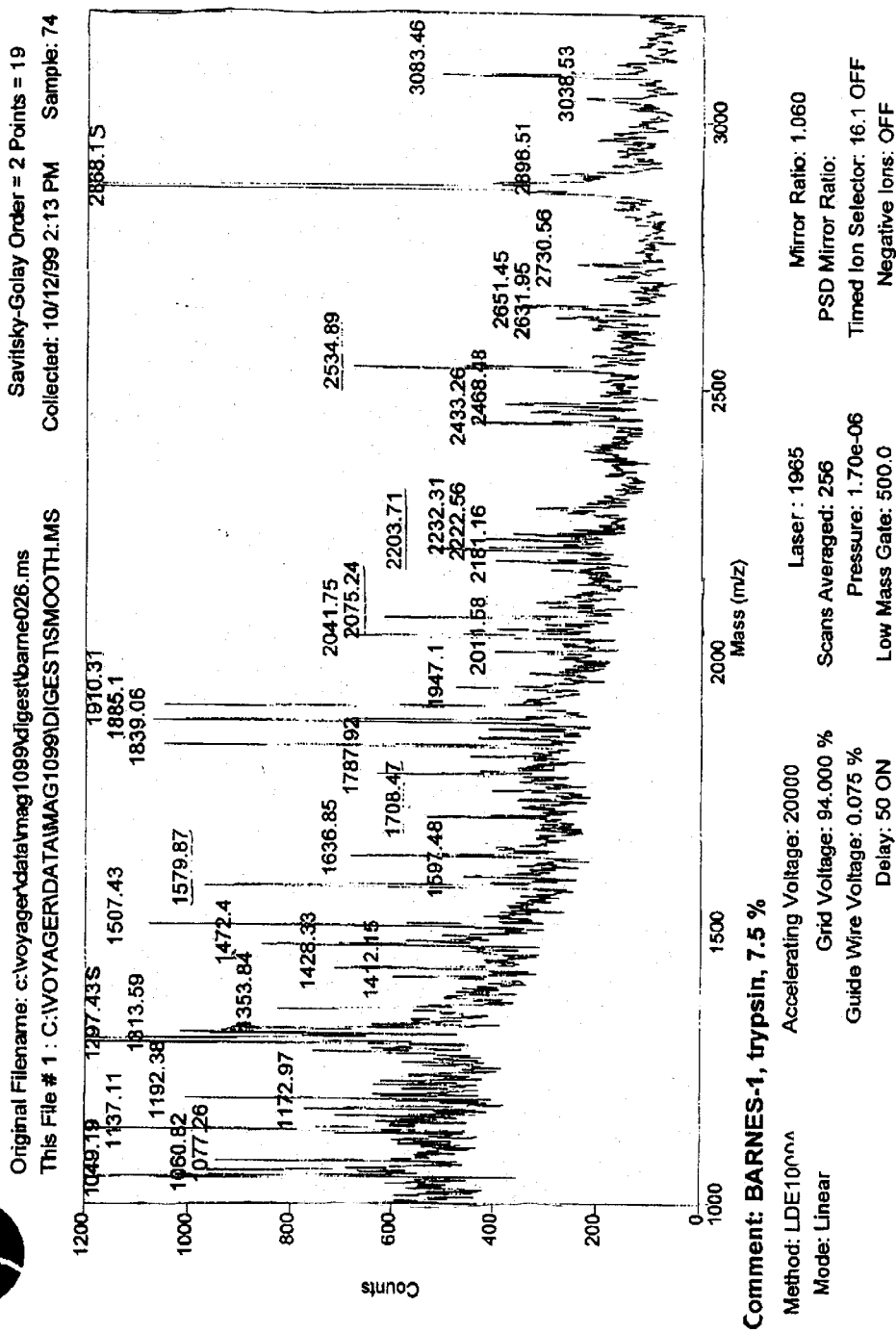
Figure 7A (Band 1)

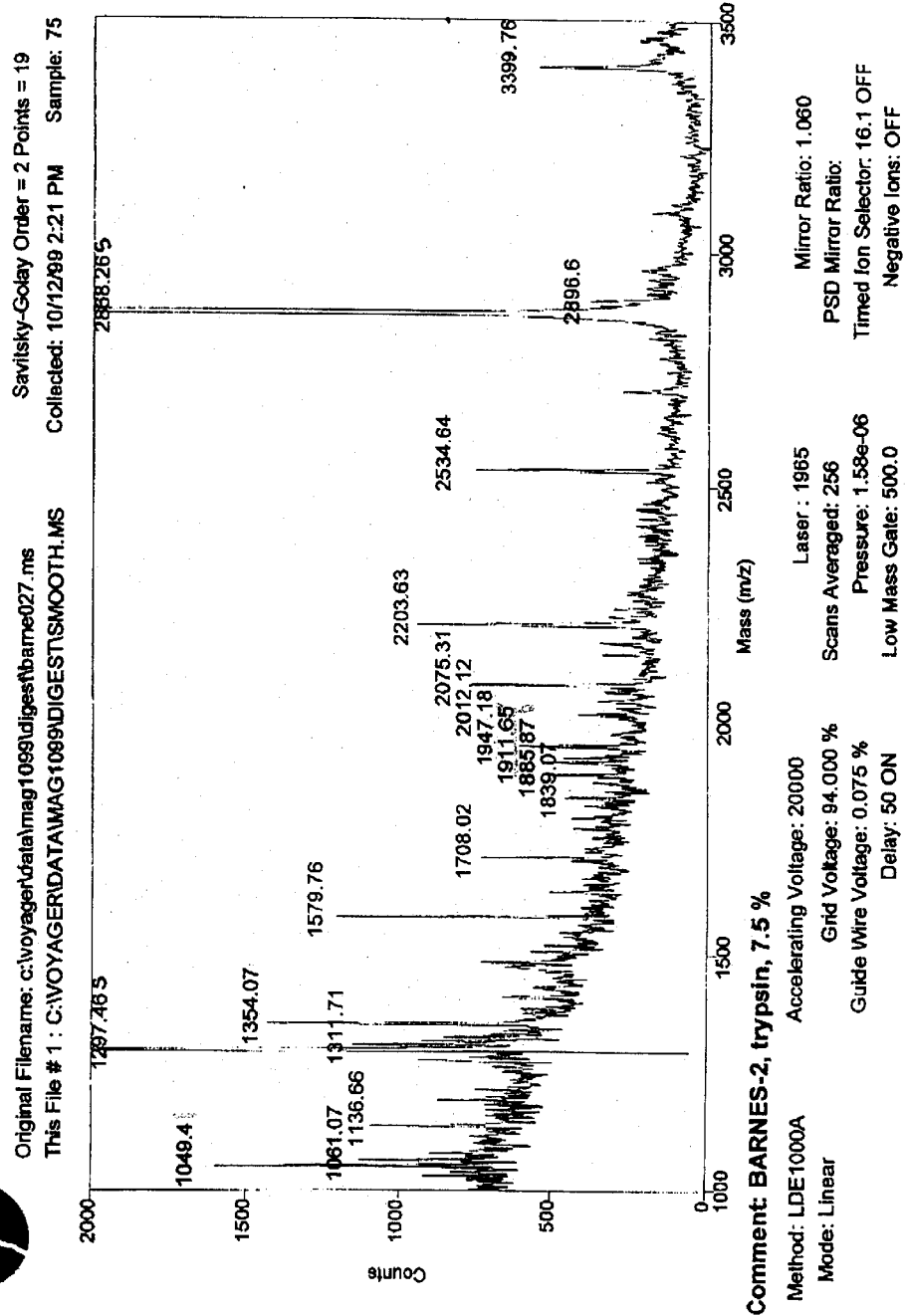
Figure 7B (Band 2)

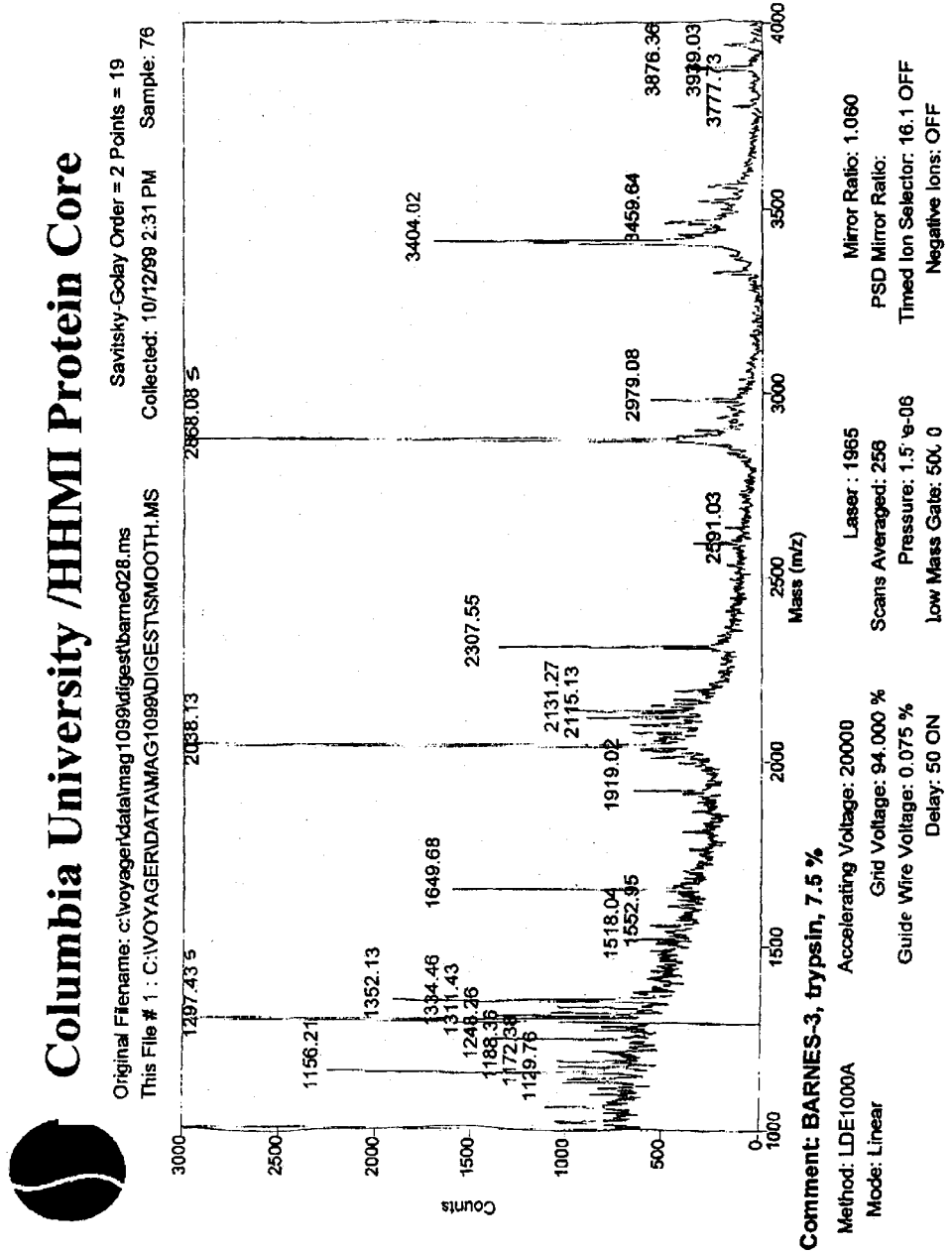
Figure 7C (Band 3)

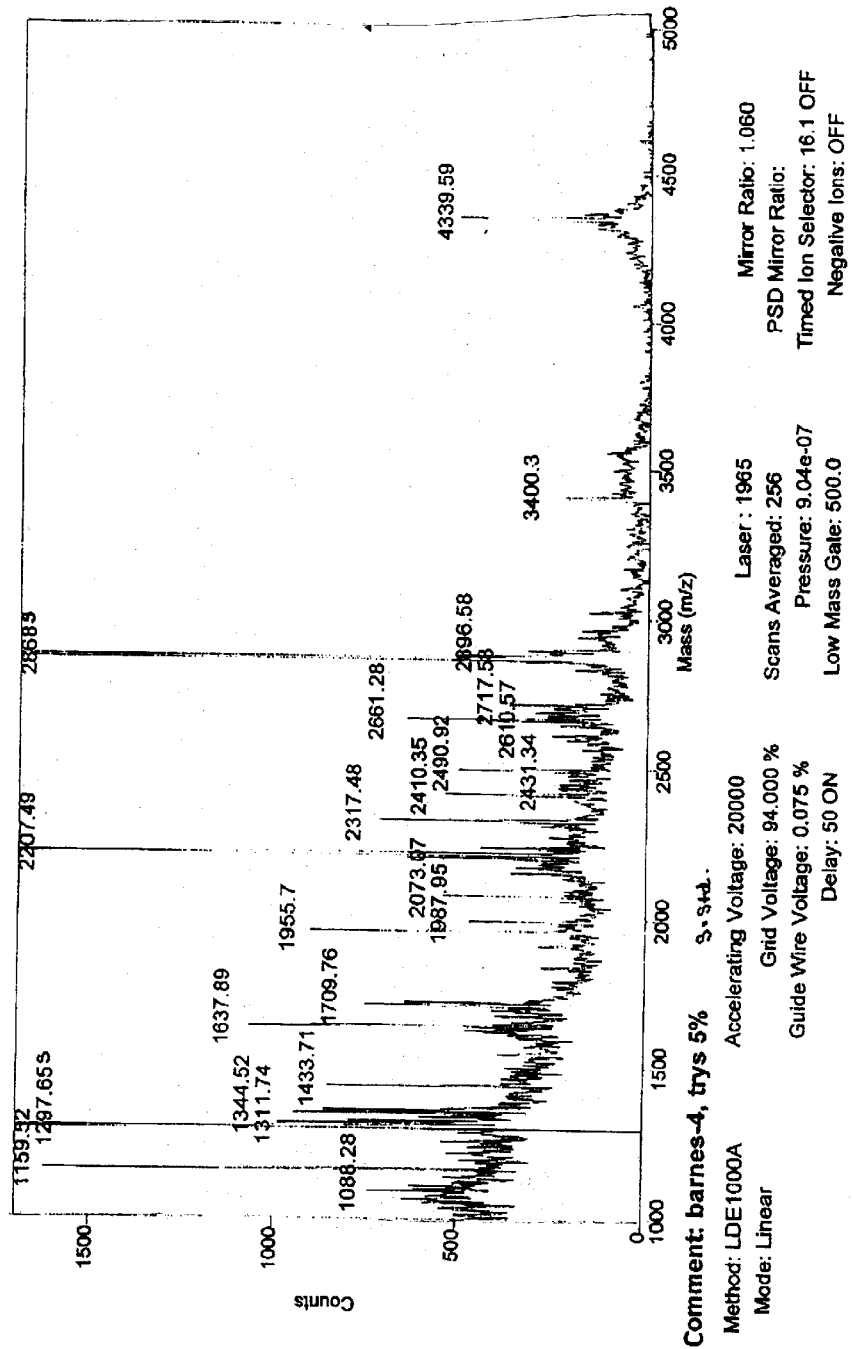
Figure 7D (Band 4)

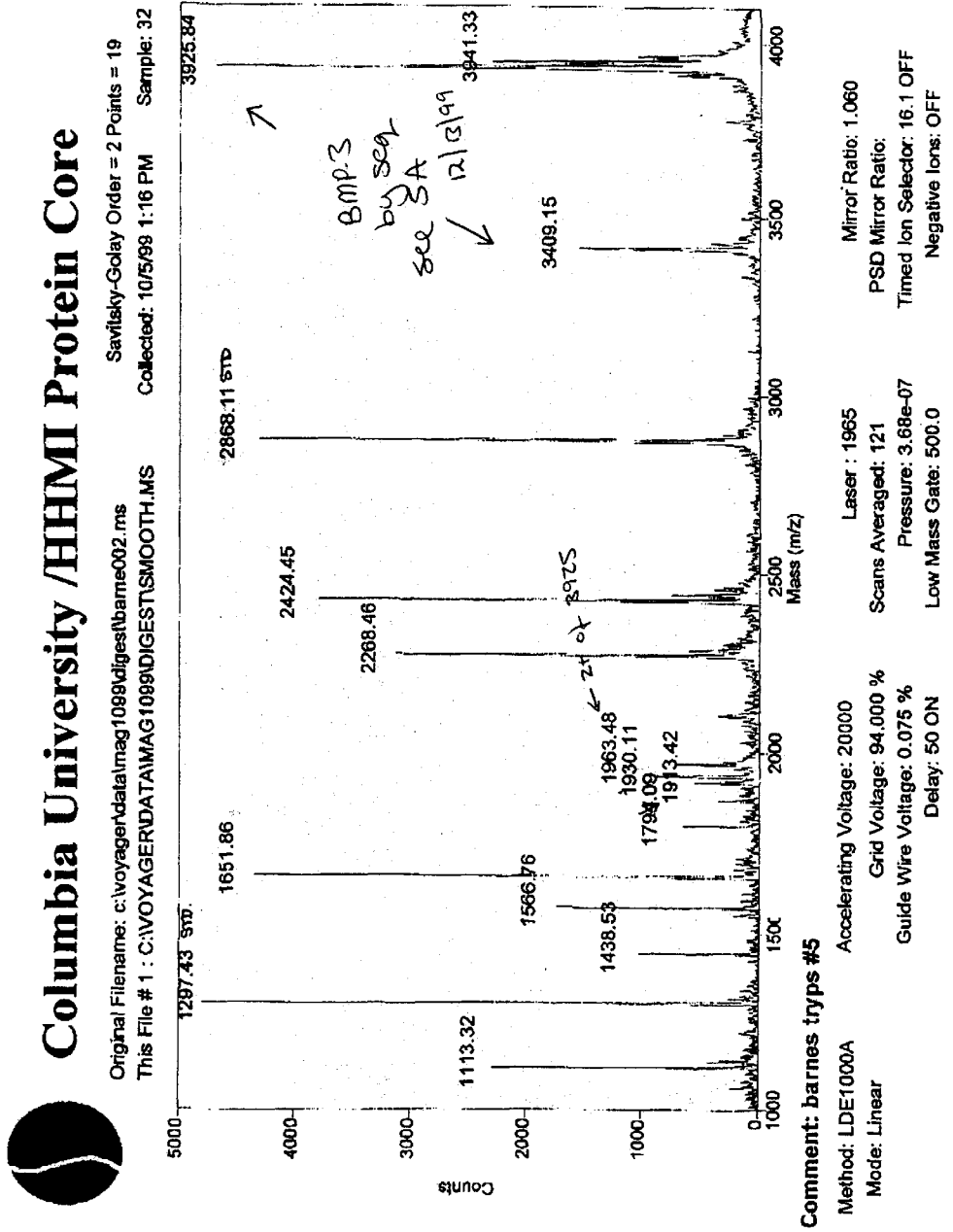
Figure 7E (Band 5)

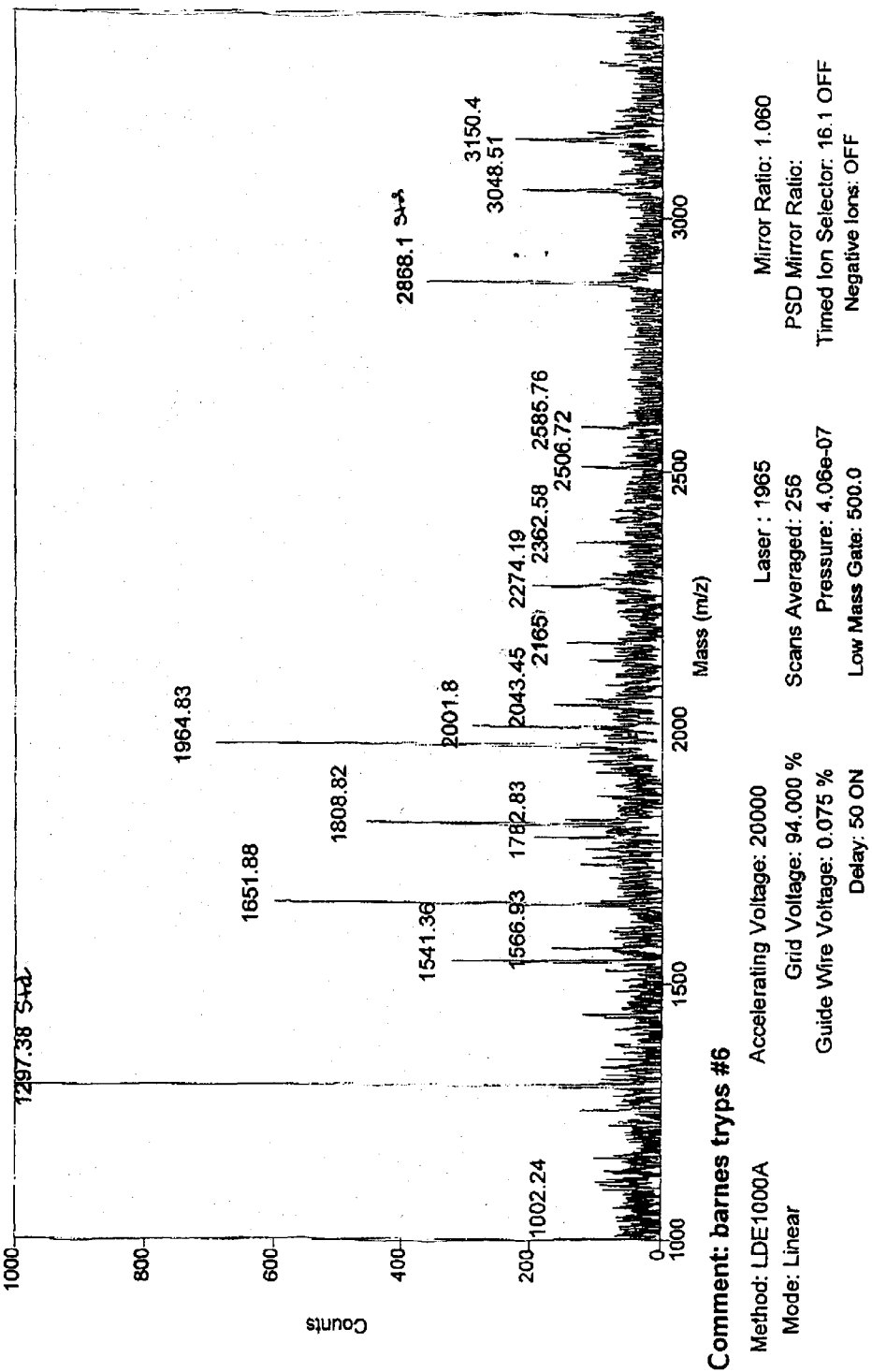
Figure 7F (Band 6)

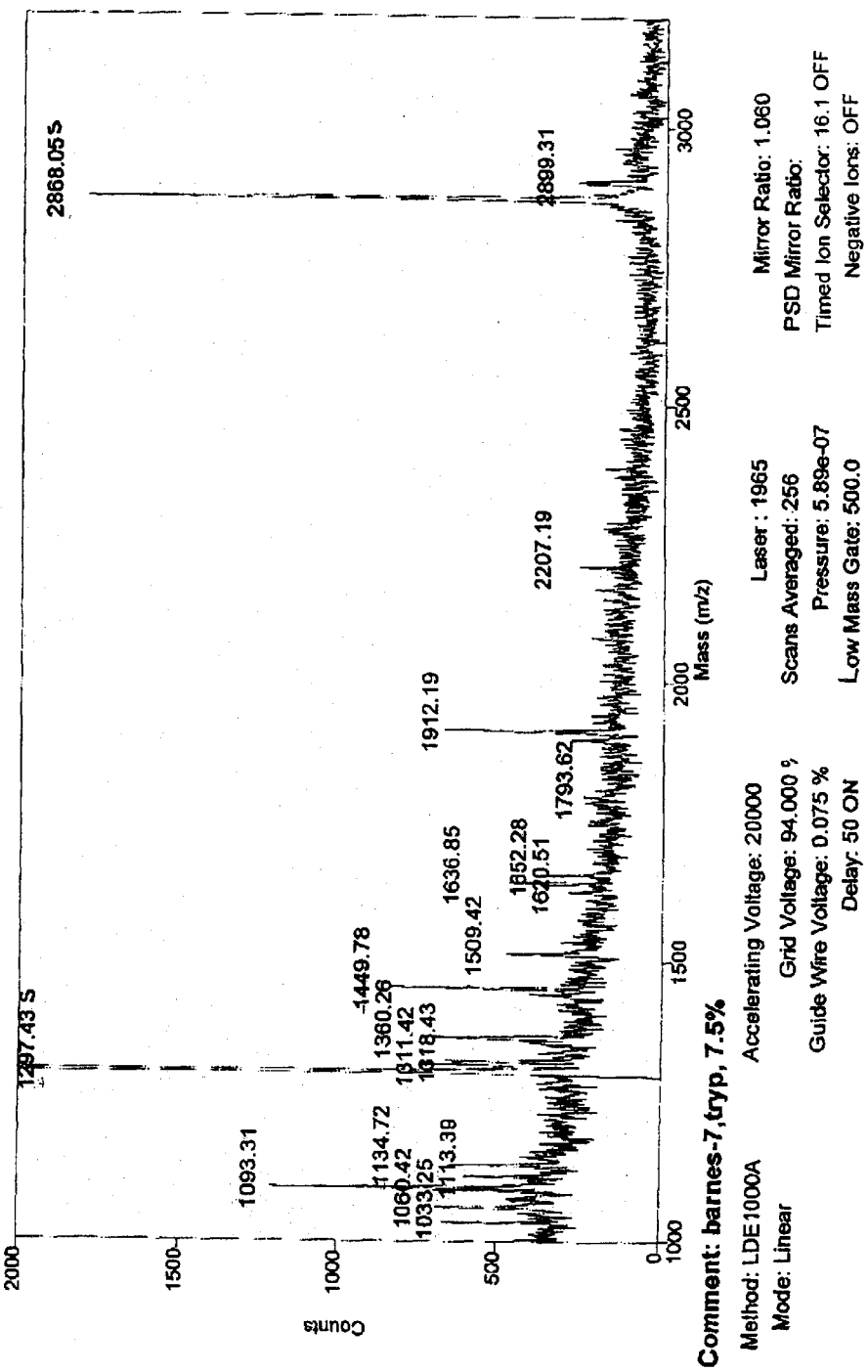
Figure 7G (Band 7)

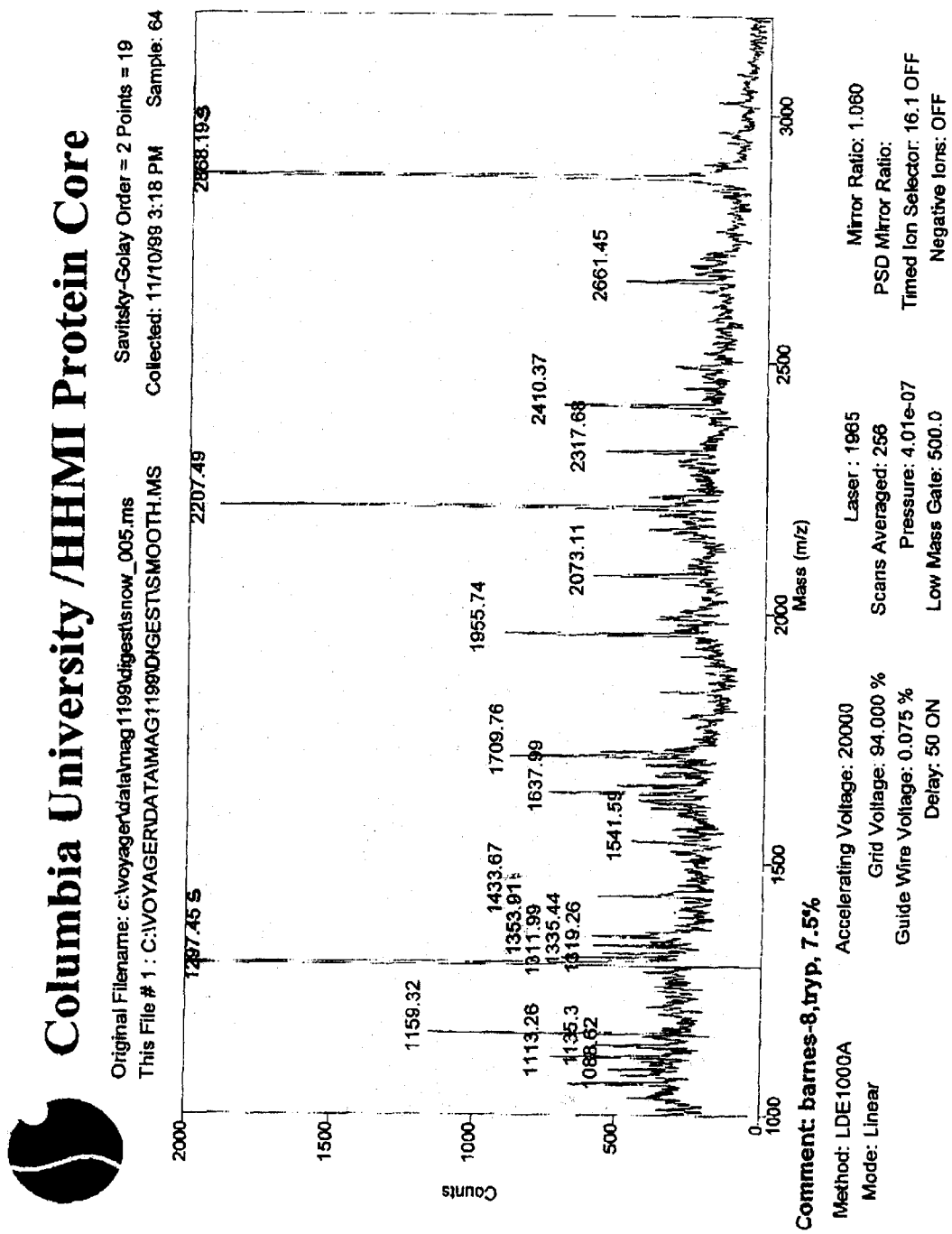
Figure 7H (Band 8)

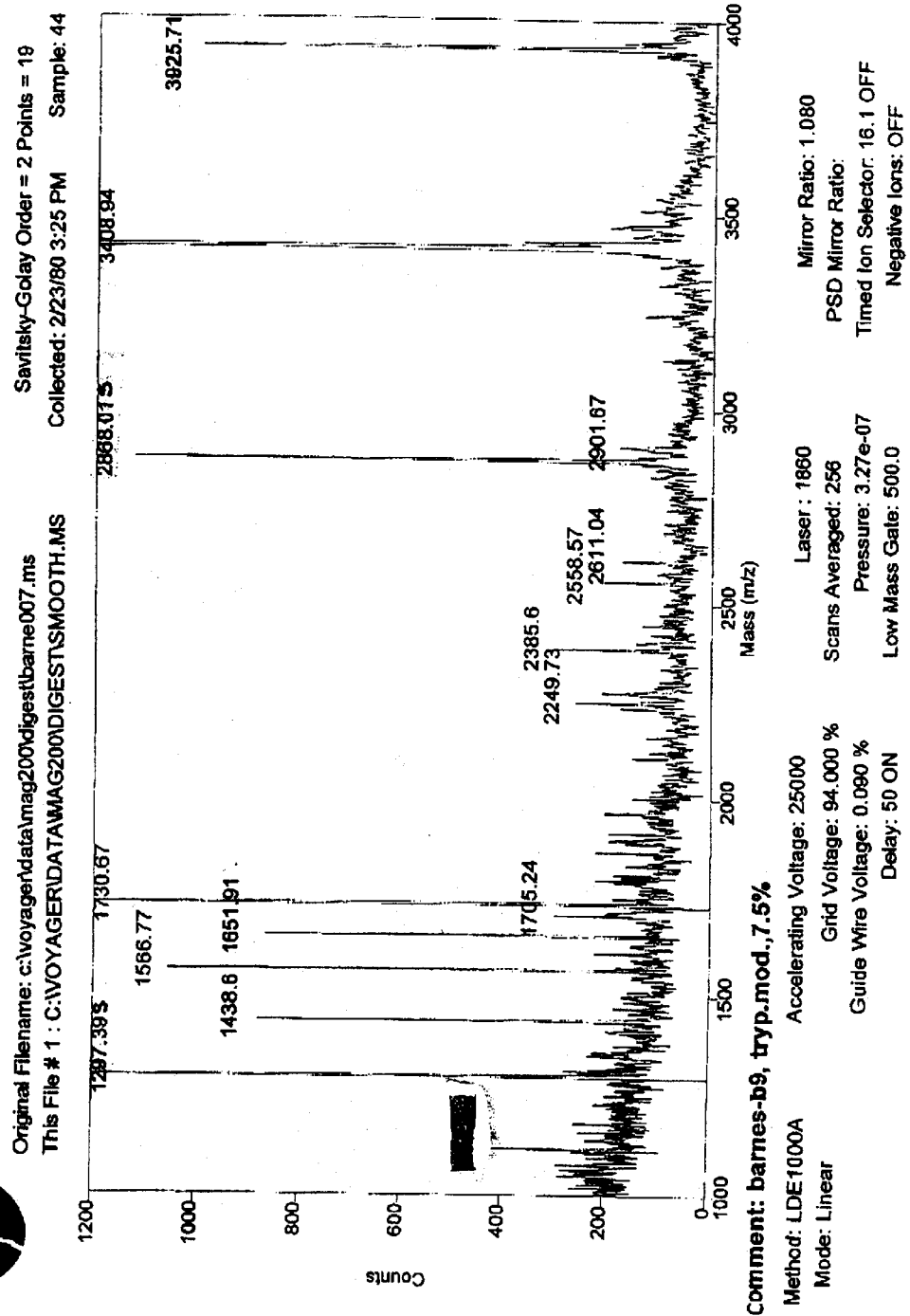
Figure 7I (Band 9)

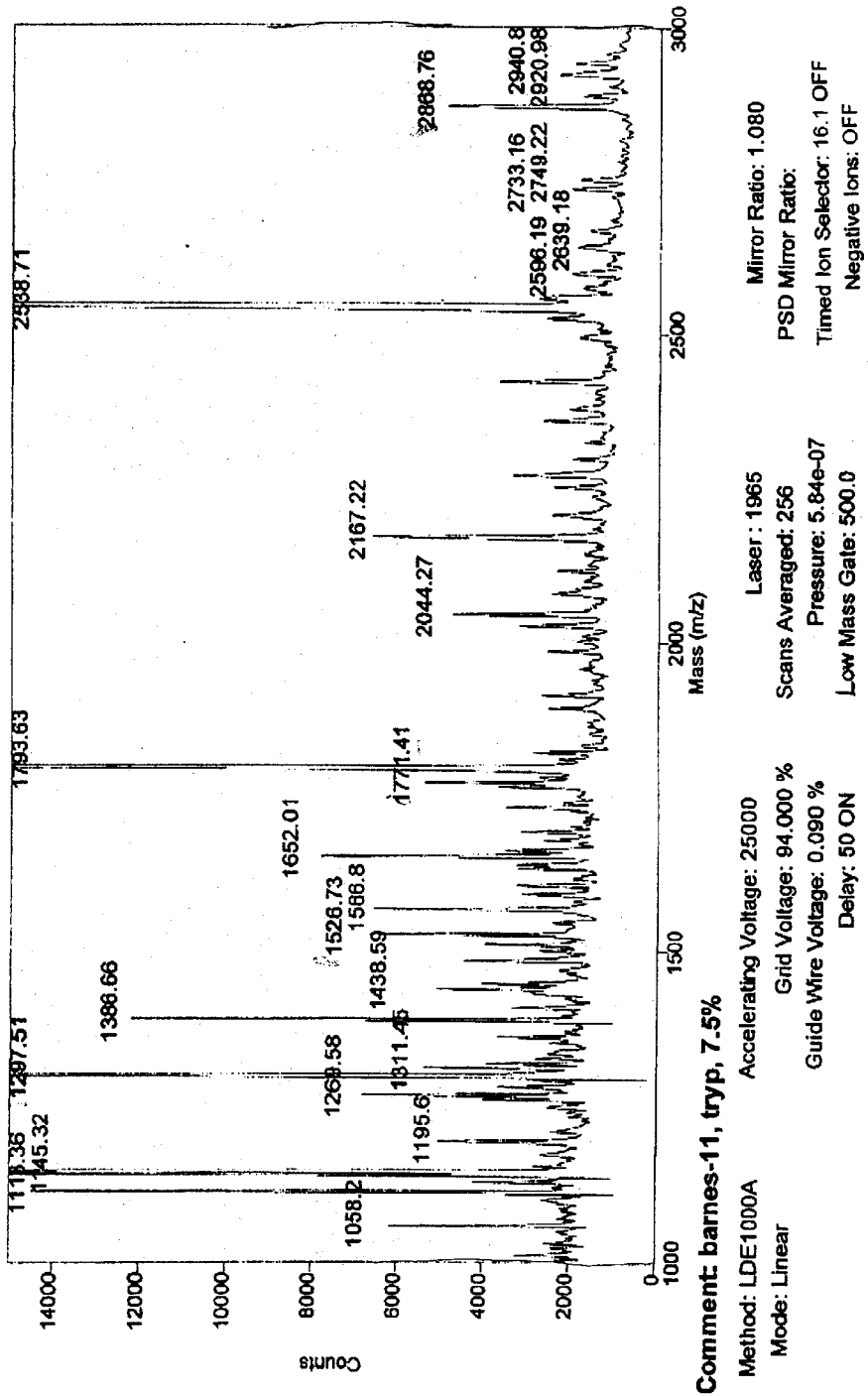
Figure 7J (Band 11)

Figure 7K (Band 18)
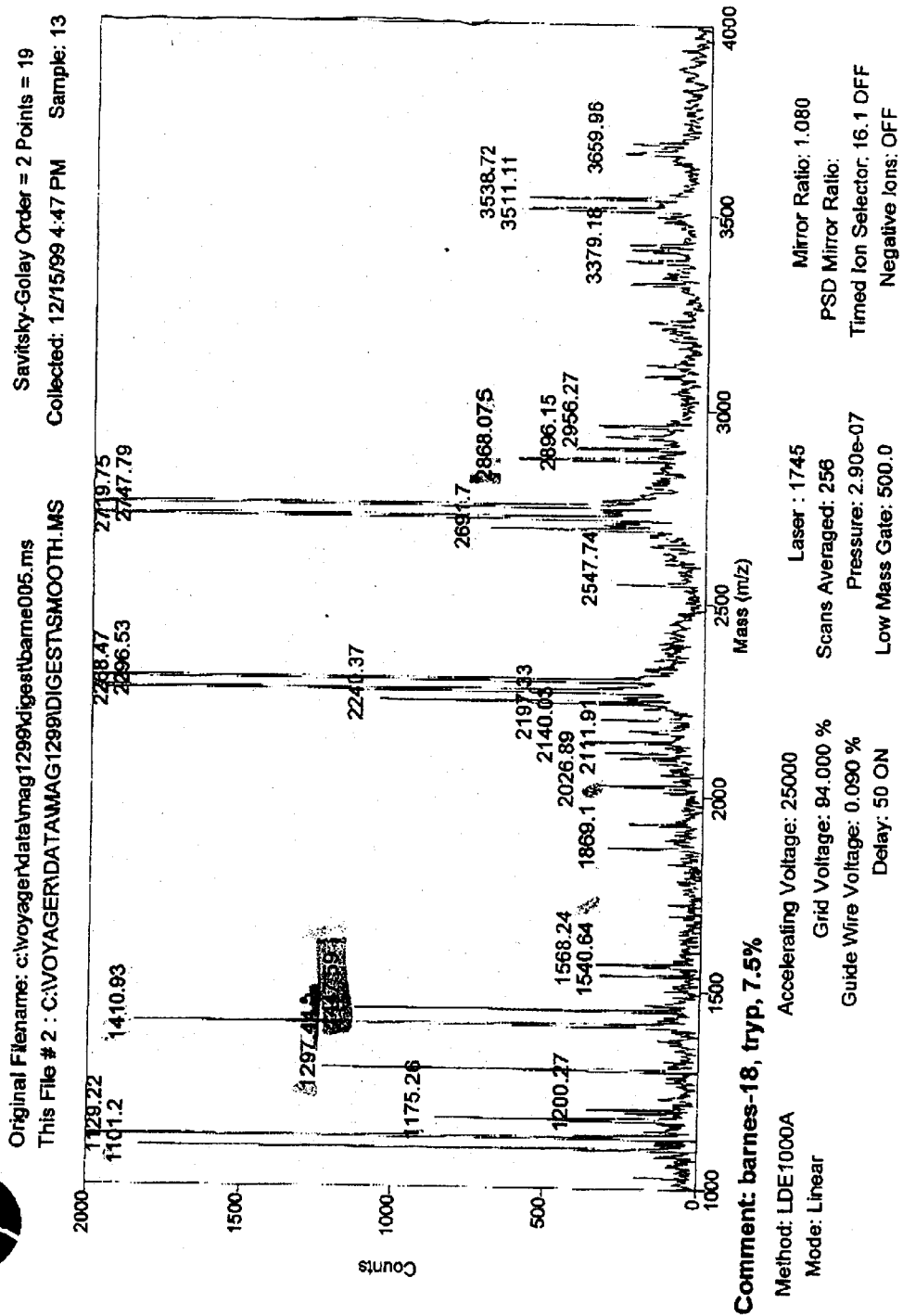

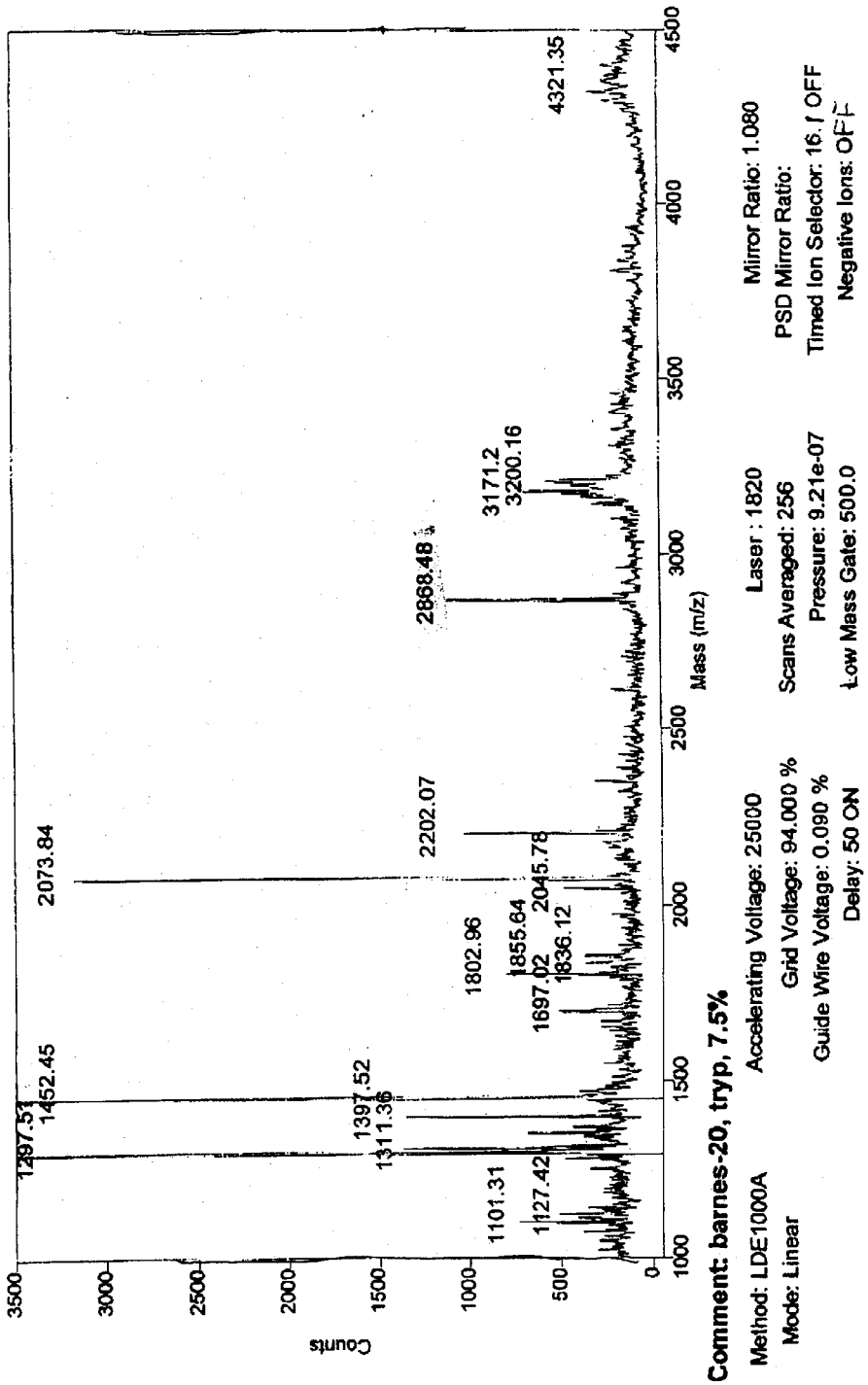
Figure 7L (Band 20)

Figure 7M (Band 22)
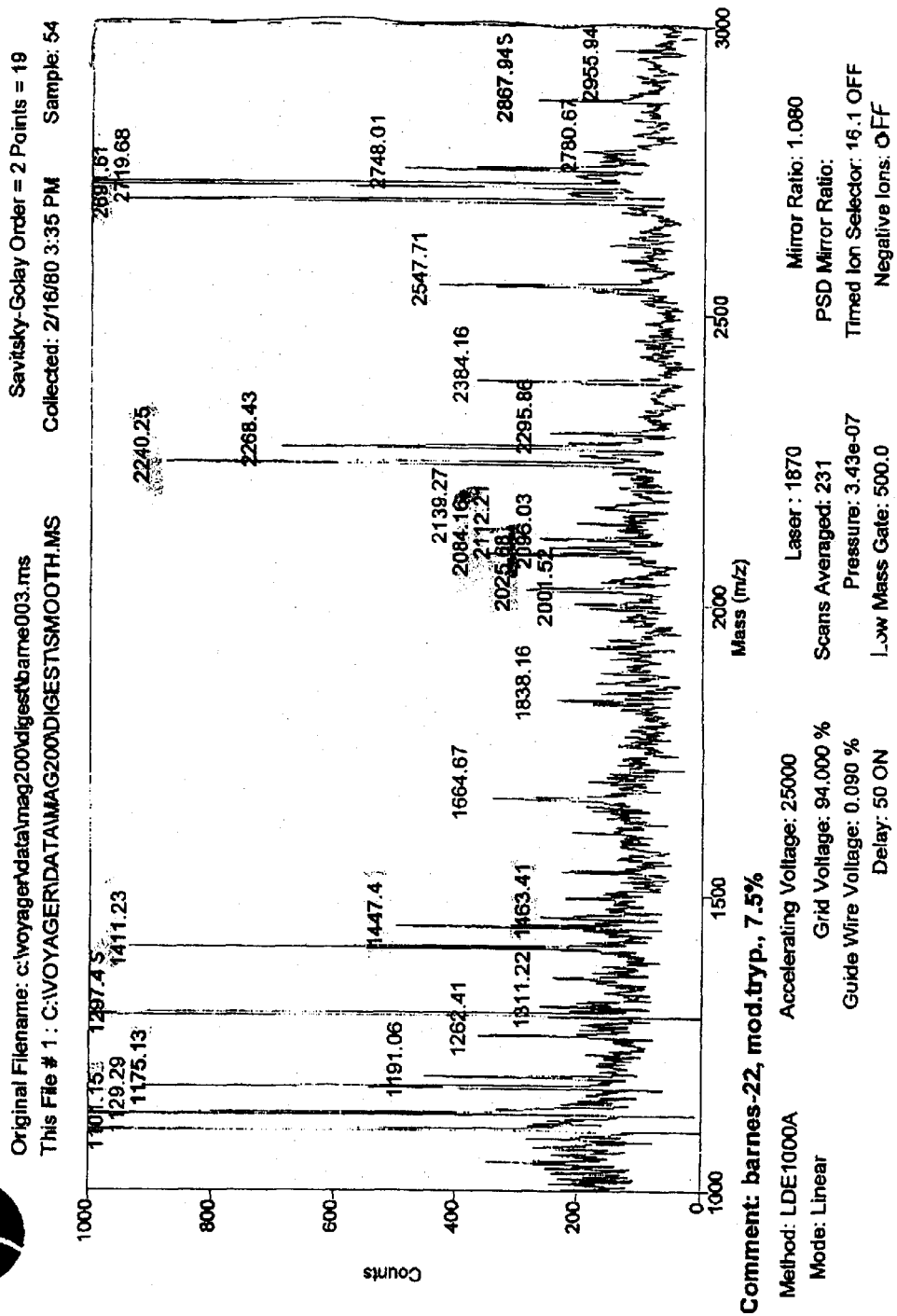

Figure 7N (Band 25)
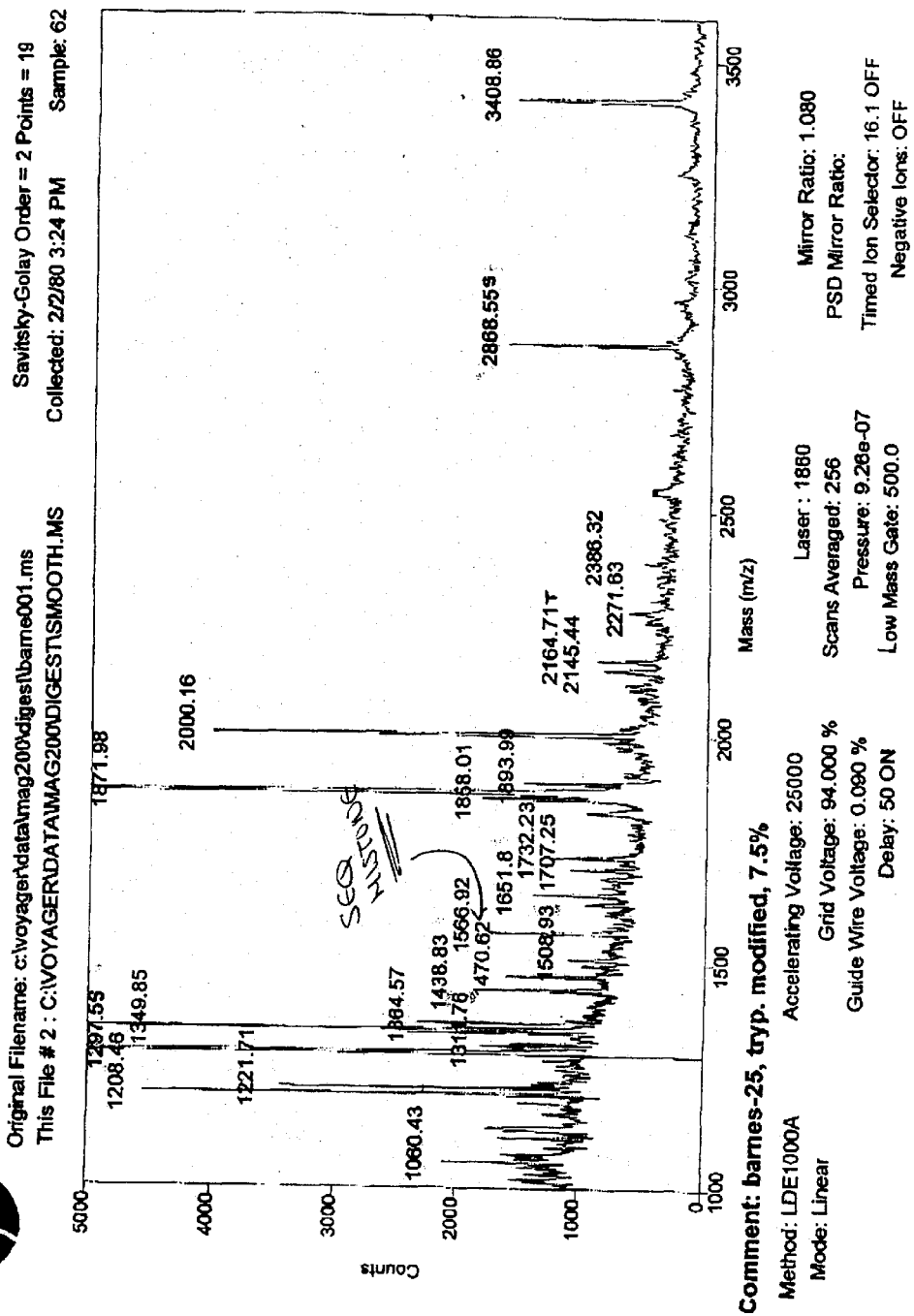

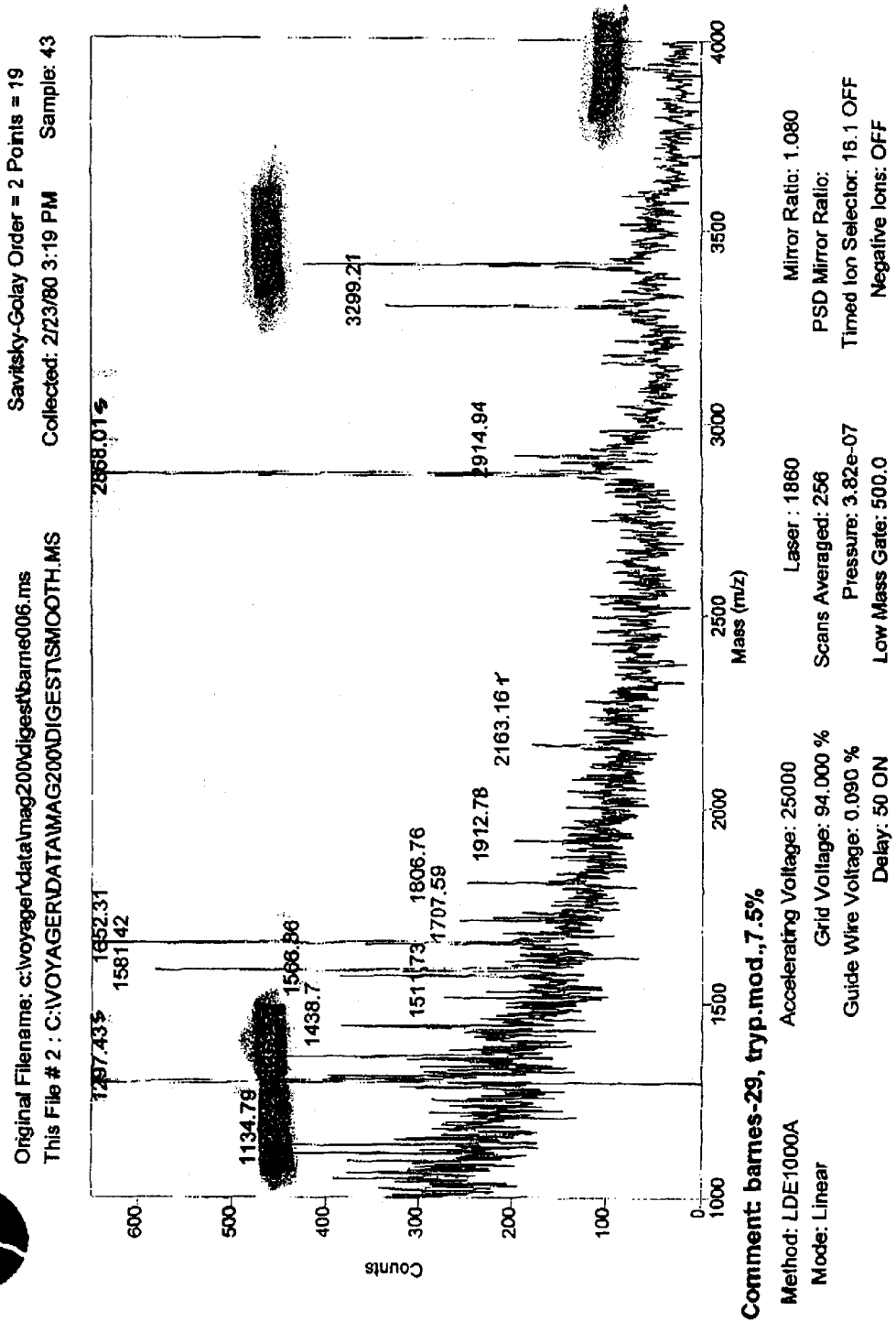
Figure 7O (Band 29)

FIGURE 10
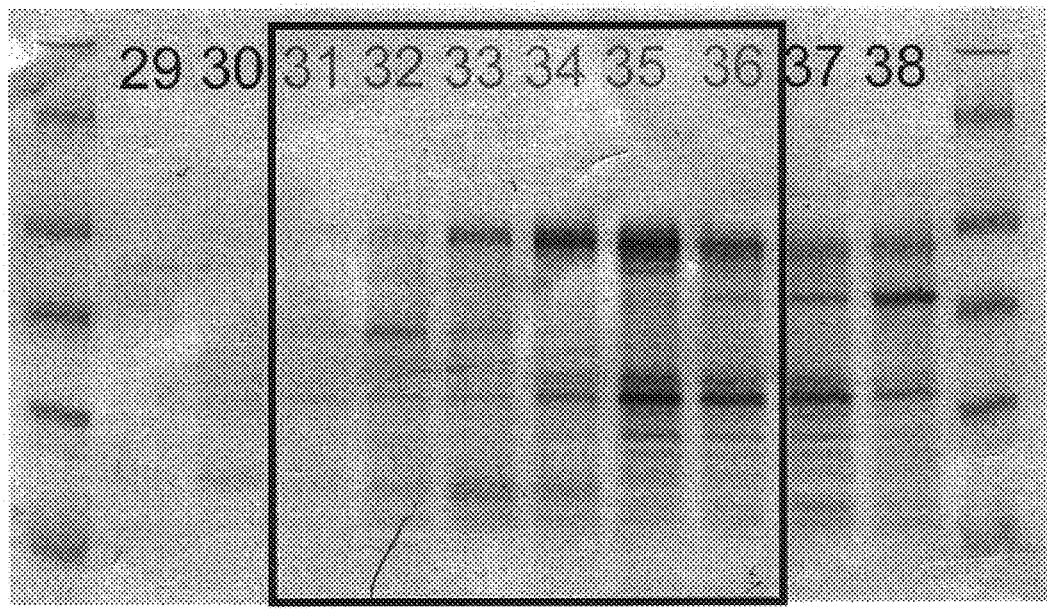
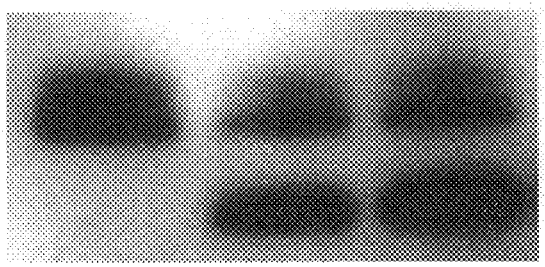
FIGURE 11
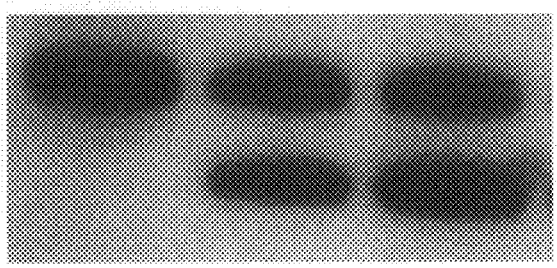
FIGURE 12

FIGURE 13A
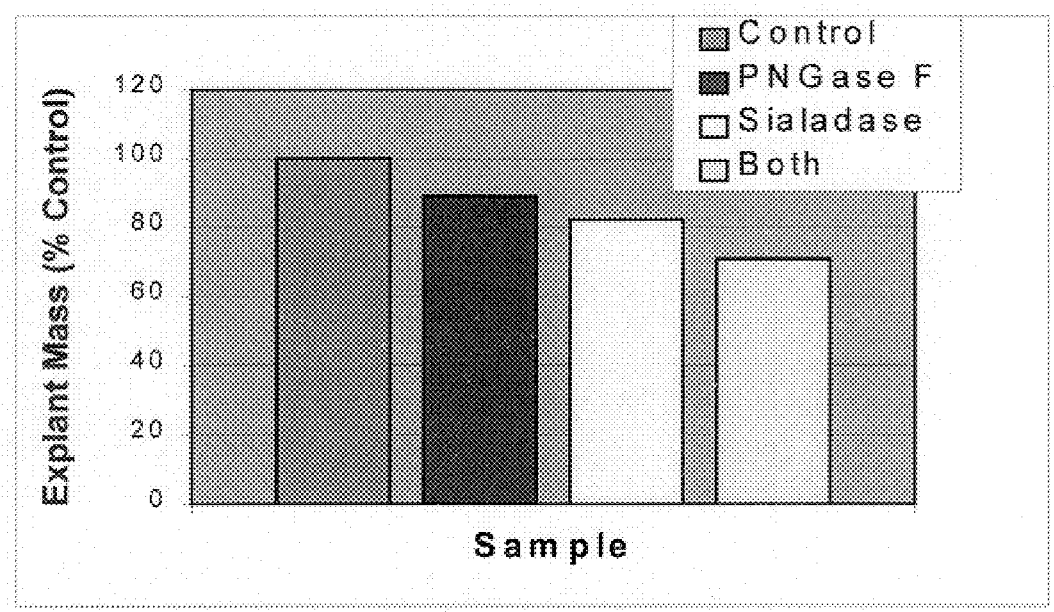
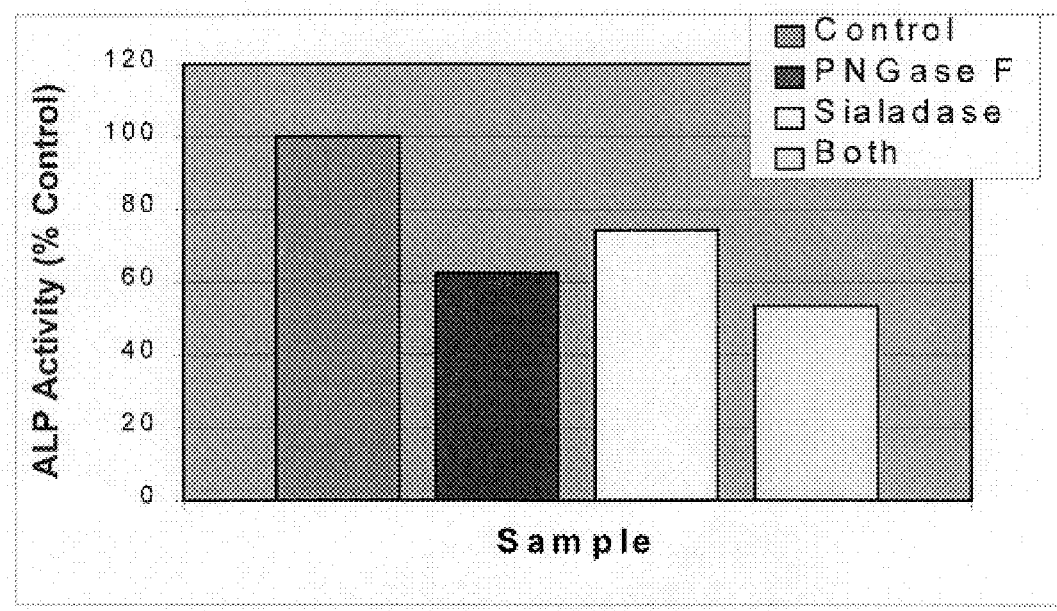
FIGURE 13B

FIGURE 14: Antibody Listing

| Specificity | Antigen | Host Species | PC/MC | Source | Catalog No. |
|---|---|---|---|---|---|
| TGF-β1 (human) | Protein | Rabbit | Polyclonal | Promega | G1221 |
| TGF-β2 (human) | Peptide | Rabbit | Polyclonal | Santa Cruz Biotechnology | sc-90 |
| TGF-β3 (human) | Peptide | Rabbit | Polyclonal | Santa Cruz Biotechnology | sc-82 |
| | | | | | |
| BMP-2 (human) | Protein | Rabbit | Polyclonal | Austral Biologics | PA-513-9 |
| BMP-3 (human) | Peptide | Chicken | Polyclonal | Research Genetics | NA |
| BMP-4 (human) | Peptide | Goat | Polyclonal | Santa Cruz Biotechnology | so-6896 |
| BMP-5 (human) | Peptide | Goat | Polyclonal | Santa Cruz Biotechnology | sc-7405 |
| BMP-6 (human) | Peptide | Mouse | Monoclonal | Novocastra Laboratories | NCL-BMP6 |
| BMP-7 (human) | Peptide | Rabbit | Polyclonal | Research Genetics | NA |
| FGF-1 (human) | Peptide | Goat | Polyclonal | Santa Cruz Biotechnology | sc-1884 |
| osteonectin (bovine) | Protein | Mouse | Monoclonal | DSHB | AON-1 |
| osteocalcin (bovine) | Protein | Rabbit | Polyclonal | Accurate Chemicals | A761/R1H |
| serum albumin (bovine) | Protein | Rabbit | Polyclonal | Chemicon International | AB870 |
| transferrin (human) | Protein | Chicken | Polyclonal | Chemicon International | AB797 |
| apo-A1 lipoprotein (human) | Protein | Goat | Polyclonal | Chemicon International | AB740 |

Figure 15A: Identification of Proteins by Amino Acid Sequencing of Tryptic Fragments from 1D Gels

| Band | Sample | Sequence Data | Best Database Match | Match | Identification | Species | Accession No. | AAs |
|---|---|---|---|---|---|---|---|---|
| 1 | | | | | | | | |
| 2 | fx 49 (1579) | XLAAAGYDVEK | ALAAAGYDVEK | 11/11 | histone H1.c | human | 87668 (NCBI) | 65-75 |
| 3 | fx 67 (1346) | SLEKVCADLIR | SLEKVCADLIR | 11/11 | 40s Ribosomal Protein S20 | rat | R3RT20 (PIR) | 31-41 |
| 4 | fx 65 () | (V)VCGMLGFPSEAPV | VVCGMLGFPGEKRV | 11/14 | LORP | mouse | AAC95338 (NCBI) | 213-226 |
| 5 | N terminal seq | STGVLLPLQNNELPG | STGVLLPLQNNELPG | 15/15 | BMP-3 | human | 4557371 (NCBI) | 290-304 |
| | fx 72 (3925) | STGVLLPLQNNELPGAEYQY | STGVLLPLQNNELPGAEYQY | 20/20 | BMP-3 | human | 4557371 (NCBI) | 290-309 |
| | fx 74 (3409) | STGVLLPLQ | STGVLLPLQ | 9/9 | BMP-3 | human | 4557371 (NCBI) | 290-298 |
| 6 | fx 55 (1566) | (S)SQTLQFXE | SQTLQFDE | 7/8 | BMP-3 | human | 4557371 (NCBI) | 346-353 |
| | fx 47 | VYAF | no match | | ??? | | | |
| | N terminal seq | HAGKYSREKNT(P)A(P) | HGGKYSREKNQPKP | 11/14 | α2-Macroglobulin Receptor Assoc. Pro. | human | P30533 (Swiss-Prot) | 31-46 |
| | fx 57 (1438) | SQTLQFDEQ | SQTLQFDEQ | 9/9 | BMP-3 | human | 4557371 (NCBI) | 346-354 |
| | fx 57 (1652) | SLKPSNHA | SLKPSNHA | 8/8 | BMP-3 | human | 4557371 (NCBI) | 410-417 |
| 7 | fx 51 (1093) | AALRPLVKP | AALRPLVKP | 9/9 | 60s Ribosomal Protein L32 | mouse | P17932 (Swiss-Prot) | 1-9 |
| | fx 37 (no MS) | A(H)I(Q)VERYV | AIVER | 5/5 | 60s Ribosomal Protein L32 | mouse | P17932 (Swiss-Prot) | 109-113 |
| | fx 37 (no MS) | A(H)I(Q)VERYV | HQSDRYV | 5/7 | ??? | | | 22-28 |
| 8 | fx 78 () | XALF(G)AQLGXALGPI | no match | | | | | |
| 9 | fx 56 (1567) | SQTLQFDEQT | SQTLQFDEQT | 10/10 | BMP-3 | human | P12645 (Swiss-Prot) | 346-355 |

Figure 15B: Identification of Proteins by Amino Acid Sequencing of Tryptic Fragments from 1D Gels

| Band | Sample | Sequence Data | Best Database Match | Match | Identification | Species | Accession No. | AAs |
|---|---|---|---|---|---|---|---|---|
| 11 | fx 55 (1311) | SQTLXF | SQTLQF | 5/6 | BMP-3 | human | 4557371 (NCBI) | 346-351 |
|  | fx 47 (1772) | VLATVTKPVGGDK | VLATVTKPVGGDK | 13/13 | 60s Ribosomal Protein L6 | human | Q02878 (Swiss-Prot) | 87-99 |
|  | fx 76 (1795) | xVFAL | VFAL | 4/4 | 60s Ribosomal Protein L6 | human | Q02878 (Swiss-Prot) | 273-276 |
|  | fx 61 (1145) | AVPQLQGYLR | AIPQLQGYLR | 9/10 | 60s Ribosomal Protein L6 | human | Q02878 (Swiss-Prot) | 262-271 |
| 18 |  |  |  |  |  |  |  |  |
| 22 | fx 58 (1101) | ALDAAYCFR | ALDAAYCFR | 9/9 | TGF-β2 | human | P08112 (Swiss-Prot) | 303-311 |
|  | fx 69 (no match) | GYNANFCAGACPYL | GYNANFCAGACPYL | 14/14 | TGF-β2 | human | P08112 (Swiss-Prot) | 340-353 |
|  | fx 66 (1411.71) | VNSQSLSPY | VNSQSLSPY | 9/9 | SPP24 | bovine | Q27967 (Swiss-Prot) | 42-50 |
| 25 | fx 39 (1470) | KAAKPSV(P) | KAAKPSVP | 8/8 | Histone H1.x | human | JC4928 (PIR) | 199-206 |
| 29 |  |  |  |  |  |  |  |  | fx=fraction number (molecular weight of fragment, as measured by SDS-PAGE)

Figure 16A: Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 1 | 4 peaks match with histone H1.c | human | 87668 (NCBI) | 1172.97 | 1172.37 | 0.60 | 110-121 | 22 | 15 MS peaks match with Band 2 |
| | | | | 1579.87 | 1579.71 | 0.16 | 65-79 | | |
| | | | | 1708.47 | 1707.89 | 0.58 | 64-79 | | |
| | | | | 2011.58 | 2012.32 | -0.74 | 35-54 | | |
| 2 | 3 peaks match with histone H1.c | human | 87668 (NCBI) | 1579.76 | 1579.71 | 0.05 | 65-79* | 16 | identification of starred peptide confirmed by sequence analysis |
| | | | | 1708.02 | 1707.89 | 0.13 | 64-79 | | 15 MS peaks match with Band 1 |
| | | | | 2012.12 | 2012.32 | -0.20 | 35-54 | | |
| 3 | 7 peaks match with ribosome S20 | rat | R3RT20 (PIR) | 1129.76 | 1129.40 | 0.36 | 50-59 | 62 | |
| | | | | 1156.21 | 1156.30 | -0.09 | 76-83 | | |
| | | | | 1334.46 | 1334.62 | -0.16 | 56-66 | | |
| | | | | 1352.13 | 1351.58 | 0.55 | 88-99 | | |
| | | | | 1518.04 | 1517.77 | 0.27 | 9-21 | | |
| | | | | 1919.02 | 1919.19 | -0.17 | 5-21 | | |
| | | | | 3404.02 | 3404.87 | -0.85 | 88-119 | | |
| 4 | 3 peaks match with Lysyl Oxidase RP | human | NP002309 (Swiss-Prot) | 1987.95 | 1988.27 | -0.32 | 150-167 | 6 | 12 MS peaks match with Band 8 |
| | | | | 2410.35 | 2410.63 | -0.28 | 648-669 | | |
| | | | | 2610.57 | 2610.10 | 0.47 | 455-478 | | |

Figure 16B: Identification of Proteins by Mass Spectrometry of Tryptic Fragments from 1D Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 5 | 9 peaks match with BMP-3 | human | 4557371 (NCBI) | 1113.32 | 1113.31 | 0.01 | 361-368 | 48 | % coverage calculation is relative to the mature BMP-3, 183 AAS (290-472) |
| | | | | 1438.53 | 1438.58 | -0.05 | 346-357 | | |
| | | | | 1566.76 | 1566.76 | 0.00 | 345-357 | | |
| | | | | 1651.86 | 1651.91 | -0.05 | 410-424 | | |
| | | | | 1794.09 | 1794.02 | 0.07 | 346-360 | | |
| | | | | 2268.46 | 2268.63 | -0.17 | 374-392 | | |
| | | | | 2424.45 | 2424.81 | -0.36 | 373-392 | | |
| | | | | 3409.15 | 3407.77 | 1.38 | 290-318* | | Identification of starred peptide confirmed by sequence analysis |
| 6 | 3 peaks match with α2-Macroglobulin RAP | human | P30533 (Swiss-Prot) | 1002.24 | 1002.15 | 0.09 | 283-290 | 17 | |
| | | | | 2362.58 | 2362.43 | 0.15 | 129-150 | | |
| | | | | 3048.51 | 3048.52 | -0.01 | 257-282 | | |
| | 2 peaks match with BMP-3 | human | 4557371 (NCBI) | 1566.93 | 1566.75 | 0.18 | 346-357 | 15 | % coverage calculation is relative to the mature BMP-3, 183 AAS (290-472) |
| | | | | 1651.88 | 1651.91 | -0.03 | 410-424 | | |

Figure 16C: Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 7 | 4 peaks match with ribosome L32 | mouse | P17932 (Swiss-Prot) | 1033.25 | 1033.17 | 0.08 | 67-75 | 33 | |
| | | | | 1093.31 | 1093.40 | -0.09 | 1-10* | | |
| | | | | 1134.72 | 1134.28 | 0.44 | 65-74 | | |
| | | | | 1449.78 | 1449.66 | 0.12 | 19-29 | | |
| | 5 peaks match with BMP-3 | human | 4557371 (NCBI) | 1060.42 | 1060.20 | 0.22 | 102-111 | 21 | % coverage calculation is relative to the mature BMP-3, 183 AAS (290-472) |
| | | | | 1113.39 | 1113.31 | 0.08 | 361-368 | | |
| | | | | 1360.26 | 1360.58 | -0.32 | 190-200 | | |
| | | | | 1652.28 | 1651.91 | 0.37 | 410-424 | | |
| | | | | 1793.62 | 1794.02 | -0.40 | 346-360 | | |
| 8 | 1 peak matches with Lysyl Oxidase RP | human | NP002309 (Swiss-Prot) | 2410.37 | 2410.63 | -0.26 | 648-669 | 3 | 12 MS peaks match with Band 4 |
| 9 | 6 peaks match with BMP-3 | human | 4557371 (NCBI) | 1113.14 | 1113.31 | -0.17 | 361-368 | 36 | % coverage calculation is relative to the mature BMP-3, 183 AAS (290-472) |
| | | | | 1438.60 | 1438.58 | 0.02 | 346-357 | | |
| | | | | 1566.77 | 1566.76 | 0.01 | 345-357 | | |
| | | | | 1651.91 | 1651.61 | 0.30 | 410-424 | | |
| | | | | 2901.67 | 2901.19 | 0.48 | 41-66 | | |
| | | | | 3408.94 | 3407.77 | 1.17 | 290-318 | | |

Figure 16D: Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 11 | 5 peaks match with BMP-3 | human | 4557371 (NCBI) | 1113.23 | 1113.31 | -0.08 | 361-368 | 48 | % coverage calculation is relative to the mature BMP-3, 183 AAS (290-472) |
| | | | | 1651.73 | 1651.91 | -0.18 | 410-424 | | |
| | | | | 1793.58 | 1794.02 | -0.44 | 346-360 | | |
| | | | | 2424.24 | 2424.81 | -0.57 | 373-392 | | |
| | | | | 3408.34 | 3407.77 | 0.57 | 290-318 | | |
| | 5 peaks match with ribosome L6 | human | Q02878 (Swiss-Prot) | 1140.38 | 1140.23 | 0.15 | 114-122 | 16 | |
| | | | | 1526.88 | 1526.86 | 0.02 | 141-155 | | |
| | | | mouse | P47911 (Swiss-Prot) | 1059.15 | 1059.12 | 0.03 | 10-20 | | |
| | | | | 1145.36 | 1145.35 | 0.01 | 262-271 | | |
| | | | | 1386.74 | 1386.68 | 0.06 | 260-271 | | |
| 18 | 4 peaks match with TGF-β2 | human | P08112 (Swiss-Prot) | 1101.20 | 1101.26 | -0.06 | 303-311 | 52 | |
| | | | | 1175.26 | 1175.42 | -0.16 | 400-409 | | |
| | | | | 2240.37 | 2240.60 | -0.23 | 312-328 | | |
| | | | | 2691.70 | 2691.91 | -0.21 | 340-362 | | |
| | 5 peaks match with SPP24 | bovine | Q27967 (Swiss-Prot) | 1410.93 | 1411.60 | -0.67 | 42-53 | 30 | |
| | | | | 1447.59 | 1447.65 | -0.06 | 113-124 | | |
| | | | | 1540.64 | 1540.60 | 0.04 | 86-98 | | |
| | | | | 1869.10 | 1869.05 | 0.05 | 62-77 | | |
| | | | | 2268.47 | 2268.57 | -0.10 | 33-53 | | |

Figure 16E: Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 22 | 5 peaks match with TGF-β2 | human | P08112 (Swiss-Prot) | 1101.15 | 1101.26 | -0.11 | 303-311 | 63 | |
| | | | | 1175.13 | 1175.42 | -0.29 | 400-409 | | |
| | | | | 2084.16 | 2084.42 | -0.26 | 312-347 | | |
| | | | | 2240.25 | 2240.60 | -0.35 | 312-328 | | |
| | | | | 2691.61 | 2691.91 | -0.30 | 340-362 | | |
| | 2 peaks match with SPP24 | bovine | Q27967 (Swiss-Prot) | 1411.23 | 1411.60 | -0.37 | 42-53 | 11 | |
| | | | | 1447.40 | 1447.65 | -0.25 | 113-124 | | |
| 25 | 5 peaks match with histone H1.x | human | JC4928 (PIR) | 1208.46 | 1208.40 | 0.06 | 48-57 | 14 | |
| | | | | 1221.71 | 1222.35 | -0.64 | 107-118 | | |
| | | | | 1349.85 | 1350.52 | -0.67 | 107-119 | | |
| | | | | 1364.57 | 1364.59 | -0.02 | 48-58 | | |
| | | | | 1732.23 | 1732.97 | -0.74 | 43-57 | | |
| | 5 peaks match with BMP-3 | human | 4557371 (NCBI) | 1060.43 | 1060.20 | 0.23 | 102-111 | 31 | % coverage calculation is relative to the mature BMP-3, 183 AAS (280-472) |
| | | | | 1438.83 | 1438.58 | 0.25 | 346-357 | | |
| | | | | 1566.92 | 1566.76 | 0.16 | 345-357 | | |
| | | | | 1651.80 | 1651.91 | -0.11 | 410-424 | | |
| | | | | 3408.86 | 3407.77 | 1.09 | 290-318 | | |

Figure 16F: Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 29 | 4 peaks match with BMP-3 | human | 4557371 (NCBI) | 1113.22 | 1113.31 | -0.09 | 361-368 | 27 | % coverage calculation is relative to the mature BMP-3,183 AAS (290-472) |
| | | | | 1438.70 | 1438.58 | 0.12 | 346-357 | | |
| | | | | 1566.86 | 1566.75 | 0.11 | 345-357 | | |
| | | | | 3409.04 | 3407.77 | 1.27 | 290-318 | | |

FIGURE 18: Quantitation of Identified BP proteins

| Identified Protein | Percentage of Total Protein |
|---|---|
| LORP | 2 |
| BMP-3 | 11 |
| BMP-3 and A2-MG | 3 |
| RL6 & BMP-3 | 4 |
| Histone | 3 |
| Histone | 3 |
| Histone & BMP-3 | 4 |
| BMP-3 | 8 |
| RL32 & BMP-3 | 8 |
| RS2D | 5 |
| SPP24 & TGF-$\beta$2 | 6 |
| Total | 58% |

ANNULOPLASTY RING FOR REGENERATION OF DISEASED OR DAMAGED HEART VALVE ANNULUS

BACKGROUND OF THE INVENTION

1. Field of the Invention

The present invention relates to annuloplasty rings for use in the surgical correction of heart valve disorders. More particularly, the invention relates to annuloplasty rings having the capability to induce healing and/or regeneration of heart valve annular tissue.

2. Description of Related Art

Annuloplasty rings are used by surgeons to repair diseased or damaged heart valves when the disease or damage to the heart valve does not require completely replacing the natural heart valve with a heart valve prosthesis. This therapy is useful when, for example, a disease process has caused the heart valve annulus to dilate (enlarge), thereby preventing the heart valve leaflets from coapting (i.e., contacting one another) to seal against backflow of the blood through the valve.

Annuloplasty rings generally comprise a rigid or flexible ring which is sewn or stapled to the annulus of the heart valve, thereby reducing the diameter of the heart valve annulus to allow the leaflets to coapt and function properly. Since the annuloplasty technique was first implemented, several designs of annuloplasty rings or prostheses have been developed. In one of the earliest designs, a rigid ring was sewn about the valve annulus, see e.g., U.S. Pat. No. 3,656,185 (Carpentier). Other annuloplasty ring designs incorporate fully flexible rings, see e.g., U.S. Pat. No. 5,306,296 (Wright, et al.). Additional annuloplasty ring designs include various partially rigid rings and rings with rigid and flexible portions, see e.g., U.S. Pat. No. 5,061,277 (Carpentier, et al.). Most currently available annuloplasty rings are made of biocompatible fabric, such as polyester, or are a combination of materials such as a rigid core of titanium, polyethylene or silicone and a fabric cover.

A primary limitation of current therapies employing conventional annuloplasty rings or prostheses is the complete absence of any actual healing response for the heart valve tissue. Because there is no healing response, the damage to the valve is not reversed. Thus, continuation of the disease process could lead to the necessity of completely replacing the valve, with ensuing complications to the patient. Thus, surgeons may be performing complete valve replacements under current surgical protocols when valve annuloplasty alone could suffice if a healing response in the heart valve tissue could be initiated.

U.S. Pat. No. 6,024,918 (Hendriks, et al.) describes a method of making a medical device having a biomolecule immobilized on a substrate surface. Annuloplasty rings are suggested among a number of devices that could potentially be modified by attachment of a biomolecule, however no such device is specifically exemplified.

Published PCT application WO 97/16135 (Tweden et al.) discloses a fully bioresorbable annuloplasty prosthesis made of a bioresorbable polymer. Because that prosthesis, which may also include a growth factor, is completely resorbable, it is intended to be replaced by tissue over time once it is attached around a native heart valve annulus. Successful therapy using an annuloplasty ring made of completely bioresorbable material relies on an ideal scenario in which a complete healing and/or restoration of annulus competency is effected before the physical support provided to the annulus by the prosthesis is lost due to degradation. However, even determining of the ultimate degree of any healing response with any growth factor or growth factor mixture, much less accurately predicting the speed of such response, is impossible given current knowledge. One drawback of annuloplasty therapies using this kind of prosthesis in real world therapeutic applications is that resorption of the ring is can result in re-dilation of the annulus if the healing response is less than complete.

SUMMARY OF THE INVENTION

The present invention seeks to overcome these and other drawbacks inherent in the prior art by providing methods and devices for promoting actual repair and/or regeneration of diseased or damaged heart valve annulus tissue in current annuloplasty ring therapies while maintaining all of the benefits of existing valve annuloplasty therapies that employ non-resorbable rings.

Accordingly, in one embodiment, the present invention provides a non-resorbable annuloplasty ring incorporating a growth factor for regeneration of heart valve annulus tissue. In one embodiment, the invention comprises a flexible annuloplasty ring comprising an outer covering of polymeric cloth. In another embodiment, the invention comprises a rigid annuloplasty ring.

In a further embodiment, the invention comprises a non-resorbable annuloplasty ring incorporating a mixture of growth factors for regeneration of heart valve annulus tissue while providing all the benefits of existing annuloplasty ring therapy. The annuloplasty ring may comprise a rigid or flexible ring, and may incorporate an inner polymeric member.

In yet another embodiment, the invention comprises a non-resorbable annuloplasty ring comprising a first growth factor reservoir for rapid release into the heart valve tissue and a second growth factor reservoir for relatively slower release into the heart valve tissue. The first growth factor reservoir may comprise a cloth outer covering of the annuloplasty ring or an inner fabric or foam member. The second growth factor reservoir may comprise a degradable or resorbable polymer containing a growth factor.

In another embodiment, the invention comprises a non-resorbable annuloplasty ring comprising a flexible annuloplasty ring having a cloth covering comprising a growth factor mixture and a resorbable polymeric inner member comprising a growth factor mixture, the growth factor mixtures being capable of effecting a healing response in damaged valve annulus tissue. These and other embodiments, features and advantages of the present invention will become apparent with reference to the following description.

BRIEF DESCRIPTION OF THE DRAWINGS

For a more detailed description of the present invention, reference will now be made to the accompanying Figures, wherein:

FIG. 2 is an SDS-PAGE gel of HPLC fractions 27–36 of a protein mixture according to an embodiment of the present invention.

FIG. 3 is an SDS-PAGE gel with identified bands indicated according to the legend of FIG. 4;

FIGS. 7A–O are mass spectrometer results for tryptic fragments from one dimensional (1-D) gels of a protein mixture according to an embodiment of the present invention;

FIG. 9A indicates the presence of BMP-3 and BMP-2. FIG. 9B indicates the presence of BMP-3 and BMP-7. FIG. 9C indicates the presence of BMP-7 and BMP-2, and FIG. 12D indicates the presence of BMP-3 and TGF-β1;

FIG. 10 is a PAS (periodic acid schiff) stained SDS-PAGE gel of HPLC fractions of a protein mixture according to an embodiment of the present invention;

FIG. 11 is an anti-BMP-7 stained SDS-PAGE gel of a PNGase F treated protein mixture according to an embodiment of the present invention;

FIG. 12 is an anti-BMP-2 stained SDS-PAGE gel of a PNGase F treated protein mixture according to an embodiment of the present invention;

FIGS. 13A–B are bar charts showing explant mass of glycosylated components in a protein mixture according to an embodiment of the present invention (FIG. 13A) and ALP score (FIG. 13B) of the same components;

FIG. 14 is a chart showing antibody listing and reactivity;

FIGS. 15A–B together comprise a chart showing tryptic fragment sequencing data for components of a protein mixture according to an embodiment of the present invention;

FIGS. 16A–F together comprise a chart showing tryptic fragment mass spectrometry data for components of a protein mixture according to an embodiment of the present invention;

FIG. 18 is a chart illustrating the relative mass, from scanning densitometer quantification, of protein components in a protein mixture according to an embodiment of the present invention.

DETAILED DESCRIPTION OF PREFERRED EMBODIMENTS

Figure 1:
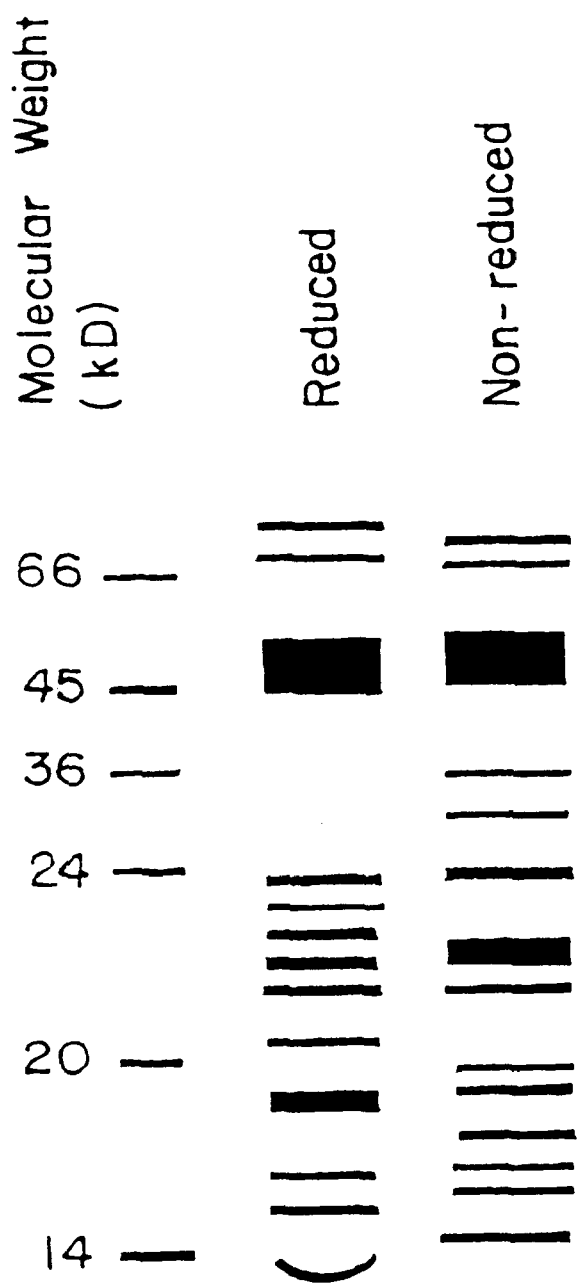
FIG. 1 illustrates an SDS-PAGE of one embodiment of the present angiogenic protein mixture, both in reduced and non-reduced forms

An improved, flexible annuloplasty prosthesis or ring that is non-resorbable and that will continue to provide support for the valve annulus over time, while also promoting healing and/or regeneration of the tissue is disclosed. Healing and/or regeneration of valvular tissue is promoted using a growth factor mixture that has been shown to be capable of promoting growth of a wide range of tissues, including heart valve tissue, and which promotes tissue growth based upon the local tissue environment (i.e., specific cell recruitment and proliferation). Thus, the present invention comprises an annuloplasty ring that provides an actual healing response in addition to providing both short- and long-term mechanical support to a dilated heart valve annulus.

Either a rigid or flexible non-resorbable annuloplasty ring may be employed to make an improved annuloplasty ring prosthesis with the above-described advantages. In addition, the ring may comprise either a full ring or a partial ring. Alternatively, a semi-rigid or partially rigid ring design may also be used. For the purposes of the present disclosure, "annuloplasty ring" or "annuloplasty prosthesis" refers to a device implanted around or in association with a mitral, tricuspid or aortic heart valve for reconstructive repair of valvular insufficiency. The term "ring" is intended to include such devices that are rounded, oval, kidney shaped, D-shaped, C-shaped or any other toroidal or partially toroidal configuration that is compatible with the configuration of a native heart valve annulus. The term "resorbable" or "bioresorbable" refers to the capability of a material to be degraded or broken down under physiological conditions into components that can be metabolized or excreted by the body.

In a preferred embodiment, a permanent or non-resorbable ring as disclosed in U.S. Pat. No. 6,102,945 (Campbell et al.) or U.S. Pat. No. 6,143,024 (Campbell et al.), both of which are hereby incorporated by reference herein in their entirety, is employed to prepare an annuloplasty ring with healing or tissue repair inductive properties. Although a number of growth factors that promote fibrous tissue growth may be suitable for combination with the desired non-resorbable or substantially non-degradable ring, it is preferred to use a growth factor mixture prepared by a process described in U.S. Patent No. 5,290,763 (Poser et al.), U.S. Pat. No. 5,371,191 (Poser et al.), or U.S. Pat. No. 5,563,124 (Damien et al.), and as described in pending U.S. patent application Ser. No. 09/545,441, particularly in Example 21 ("Characterization of BP"), the disclosures of which are incorporated by reference. In one embodiment, a mixture of growth factors prepared according to the foregoing patents is obtained from bovine bone and comprises growth factors from the Bone Morphogenetic Protein (BMP) and Transforming Growth Factor Beta (TGF-β) families including BMPs 2–7, TGFβ-1 and TGFβ-2, with BMP 3 being present in the greatest amount. The growth factor mixture is capable of proliferating a variety of different tissues, depending on the tissue environment in which it is placed, including heart valve annulus tissue.

Preferred growth factors comprise an bio-active mixture of proteins having, upon hydrolysis, an amino acid composition of from about 22.7 to about 26.2 mole percent acidic amino aids, about 45.0 to about 48.5 mole percent aliphatic amino acids, about 6.6 to about 8.4 mole percent aromatic amino acids and about 19.9 to about 22.8 mole percent basic amino acids. The growth factor may also have an amino acid composition of about 22.7 to about 26.2 mole percent of ASP (+ASN) and GLU (+GLN); about 45.0 to about 48.5 mole percent ALA, GLY, PRO, VAL, MET, ILE, and LEU; about 6.6 to about 8.4 mole percent TYR and PHE; and about 19.9 to about 22.8 mole percent HIS, ARG, and LYS. Another preferred growth factor is a protein mixture obtained by any of the purification processes described in U.S. Pat. No. 5,290,763 (Poser et al.).

A preferred angiogenic mixture of bone proteins is produced by a multi-step process that includes an ultrafiltration step, an anion exchange chromatography step, a cation exchange chromatography step and a high performance liquid chromatography (HPLC) purification step as described in detail below. Preferred processes for producing the angiogenic protein mixtures of the present invention are described in full detail in U.S. Pat. Nos. 5,290,763 and 5,371,191, which are incorporated herein in their entireties. The processes can be summarized as follows. In a first step, demineralized bone particles from a suitable source (such as crushed bovine bone) are subjected to protein extraction using guanidine hydrochloride. The extract solution is filtered, and subjected to a two step ultrafiltration process. In the first ultrafiltration step, an ultrafiltration membrane having a nominal molecular weight cut off (MWCO) of 100 kD is preferably employed. The retentate is discarded and the filtrate is subjected to a second ultrafiltration step using an ultrafiltration membrane preferably having a nominal MWCO of about 10 kD. The retentate is then subjected to diafiltration to substitute urea for guanidine. The protein-containing urea solution is then subjected to sequential ion exchange chromatography, first anion exchange chromatography followed by cation exchange chromatography. For the anion exchange process, a strongly cationic resin is used, preferably having quaternary amine functional groups. Typically, the eluant for the anion exchange process has a conductivity from about 10,260 micromhos ($\mu$mhos) (1.026×10<-2>siemens (S)) to about 11,200 $\mu$mhos (1.120× 10<31 2>S). For the cation exchange process, a strongly anionic resin is used, preferably having sulfonic acid functional groups. The eluant for the cation exchange process typically has a conductivity from about 39,100 $\mu$mhos (3.91×10<-2>S) to about 82,700 $\mu$mhos (8.27×10<-2>S) or more.

In the process described above, the proteins are advantageously kept in solution. According to the present invention, the proteins produced by the above process are then subjected to HPLC. The HPLC process preferably utilizes a column containing hydrocarbon-modified silica packing material. The proteins can be loaded onto the HPLC column in a solution of aqueous trifluoroacetic acid or other suitable solvent, such as heptafluorobutyric acid, hydrochloric or phosphoric acid. Preferably, a trifluoroacetic acid solution having a concentration of from about 0.05 percent by volume to about 0.15 percent by volume, and more preferably about 0.1 percent by volume trifluoroacetic acid is used.

Proteins are eluted from the HPLC column with an organic solvent/water mixture suitable for obtaining the desired proteins. A preferred eluant in the HPLC process is an acetonitrile solution. The preferred eluant typically has an acetonitrile concentration which varies, during elution, from about 30 percent by volume to about 45 percent by volume. In preferred embodiments, the acetonitrile concentration in the eluant is increased in increments of between about 0.30 percent by volume and about 0.40 percent by volume per minute until the desired highest concentration of acetonitrile is achieved. Proteins can be recovered from the HPLC process eluant by means generally known in the art. A preferred angiogenic fraction of the eluted proteins occurs when the acetonitrile concentration in the eluant is between about 33 percent by volume and about 37 percent by volume.

The purification processes described above yield novel angiogenic protein mixtures. Because they comprise mixtures of proteins, these angiogenic factors are most easily described in terms of their properties. Hence, in one embodiment of the present angiogenic factor, the factor is a mixture of a number of proteins having the sodium dodecyl sulfate polyacrylamide gel electrophoresis (SDS-PAGE) profile shown in FIG. 1.

Another characterization of the present invention is a mixture of proteins having a preferred amino acid composition of about 20–25 mole percent of acidic amino acids [ASP(+ASN) and GLU(+GLN)]; about 10–15 mole percent of hydroxy amino acids (SER and THR); about 35–45 mole percent aliphatic amino acids (ALA, GLY, PRO, MET, VAL, ILE, and LEU); about 4–10 mole percent aromatic amino acids (TYR and PHE); and about 10–20 mole percent basic amino acids (HIS, ARG and LYS). More particularly, this embodiment of the angiogenic protein mixture amino preferably has an amino acid composition of about 23.4 mole percent of acidic amino acids [ASP(+ASN) and GLU(+GLN)]; about 13.5 mole percent of hydroxy amino acids (SER and THR); about 40.0 mole percent aliphatic amino acids (ALA, GLY, PRO, MET, VAL, ILE, and LEU); about 6.8 mole percent aromatic amino acids (TYR and PHE); and about 16.6 mole percent basic amino acids (HIS, ARG and LYS). (TRP, CYS and ½ CYS were not measured and are not included in the calculation of mole percent.)

An alternative embodiment of the present angiogenic factor can be defined as a different fraction of the total protein stream exiting the HPLC process. More particularly, the proteins eluted when the eluant has an acetonitrile concentration of from about 37 to about 39.5 percent by volume have been found to have surprising angiogenic activity. The mixture defined in this manner contains hundreds of natural proteins. It is believed that the angiogenic activity of proteins obtained in this manner may be further enhanced by selecting smaller fractions of the eluant and quantitatively comparing the angiogenic activity of each fraction.

In addition to the foregoing, BP has been partially characterized as follows: high performance liquid chromatography (HPLC) fractions have been denatured, reduced the DTT, and separated by sodium dodecyl sulfate polyacrylamide gel electrophoresis (SDS-PAGE). One minute HPLC fractions from 27 to 36 minutes are shown in FIG. 2. Size standards (ST) of 14, 21, 31, 45, 68 and 97 kDa were obtained as Low range size standards from BIORAD™ and are shown at either end of the coomassie blue stained gel. In the usual protocol, HPLC fractions 29 through 34 are pooled to produce BP (see boxes, FIGS. 2 and 3), as shown in a similarly prepared SDS-PAGE gel in FIG. 17.

The various components of BP were characterized by mass spectrometry and amino acid to sequencing of tryptic fragments where there were sufficient levels of protein for analysis. The major bands in the ID gel (as numerically identified in FIG. 3) were excised, eluted, subjected to tryptic digestion and the fragments were HPLC purified and sequenced. The sequence data was compared against known sequences, and the best matches are shown in FIGS. 12A–B. These identifications are somewhat tentative, in that only portions of the entire proteins have been sequenced and, in some cases, there is variation between the human and bovine analogs for a given protein.

Figure 4:
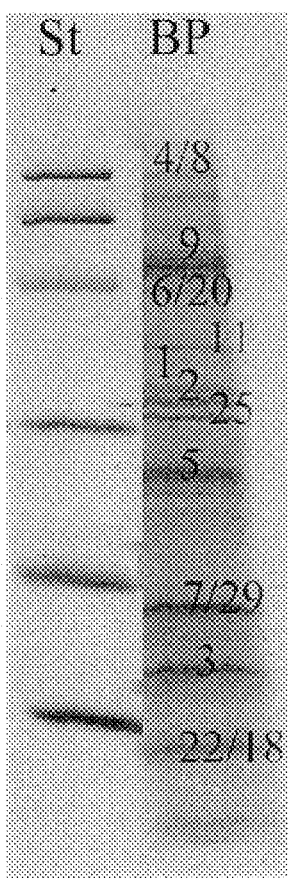
FIG. 4 is an SDS-PAGE gel of a protein mixture according to an embodiment of the present invention with identified bands indicated, as provided in the legend.

The same tryptic protein fragments were analyzed by mass spectrometry and the mass spectrograms are shown in FIGS. 7A–O. The tabulated results and homologies are shown in FIGS. 16A–F, which provide identification information for the bands identified in FIGS. 3–4. As above, assignment of spot identity may be tentative based on species differences and post translational modifications. A summary of all protein identifications for 1d gels is shown in FIG. 4.

Figure 17:
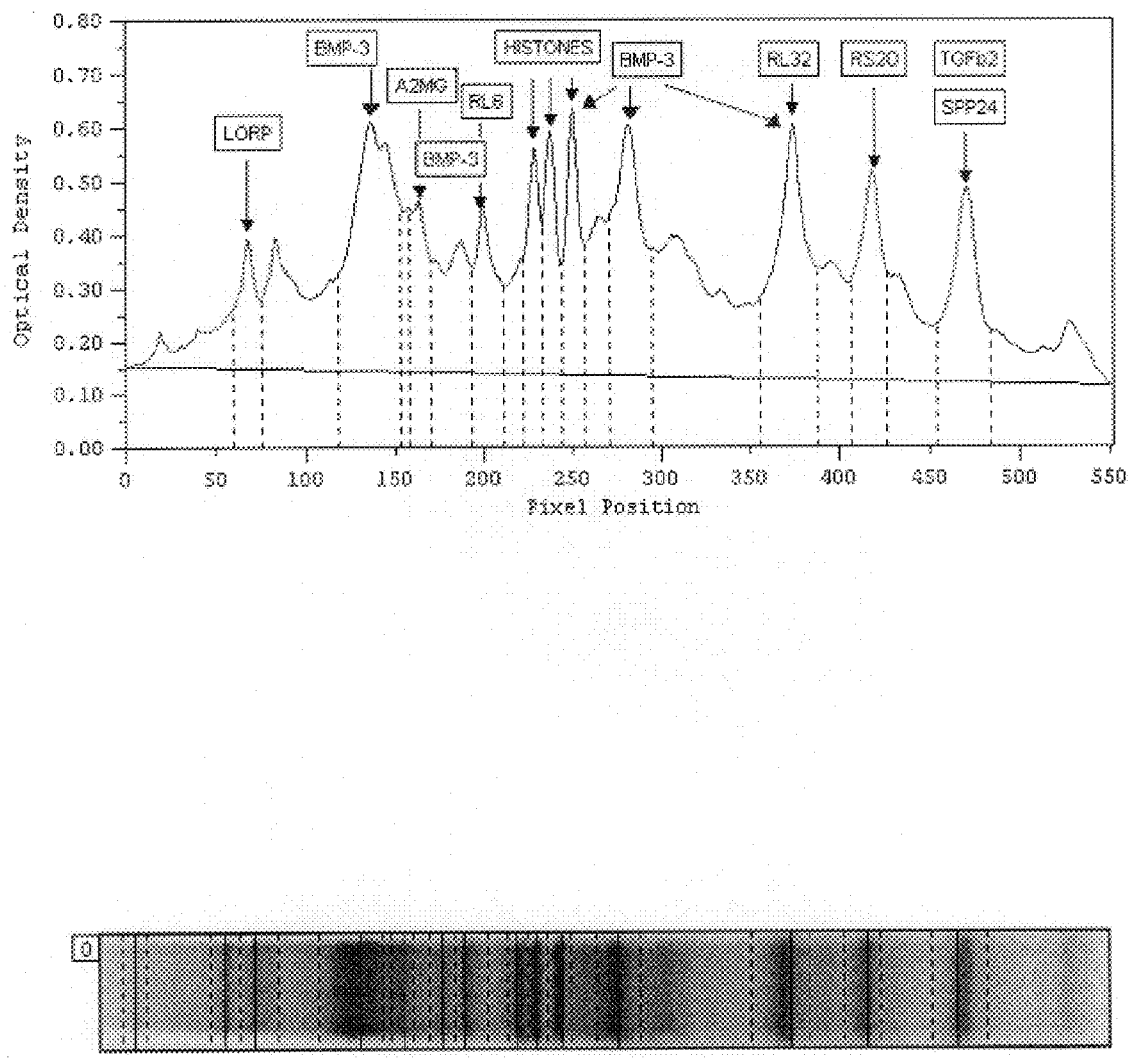
FIG. 17 is an SDS-gel (bottom portion) and a scanning densitometer scan (top portion) of the same gel for a protein mixture according to an embodiment of the present invention.

The identified protein components of BP, as described in FIGS. 15A–B, 16A–F and 19A–D, were quantified as shown in FIG. 17. FIG. 17 is a stained SDS-PAGE gel of BP and FIG. 17A represents a scanning densitometer trace of the same gel. The identified proteins were labeled and quantified by measuring the area under the curve. These results are presented in FIG. 18 as a percentage of the total peak area.

Thus, there are 11 major bands in the BP SDS-PAGE gel, representing about 60% of the protein in BP. The identified proteins fall roughly into three categories: the ribosomal proteins, the histones, and growth factors, including bone morphogenic factors (BMPs). It is expected that he ribosomal proteins may be removed from the BP without loss of activity, since these proteins are known to have no growth factor activity. Upon this separation, the specific activity is expected to increase correspondingly.

It is expected that the histone and ribosomal proteins may be removed from the BP with no resulting loss, or even with an increase, in specific activity. It is expected that histones can removed from the BP cocktail by immunoaffinity chromatography, using either specific histone protein antibodies or a pan-histone antibody. The histone depleted BP (BP-H) produced in this manner may be suitable for wound healing. Similarly, the mixture produced when the known ribosomal proteins are stripped from the BP cocktail (BP-R) may be suitable for wound healing.

An SDS-PAGE gel of BP was also analyzed by Western immunoblot with a series of antibodies, as listed in FIG. 14. Visualization of antibody reactivity was by horseradish peroxidase conjugated to a second antibody and using a chemiluminescent substrate. Further, TGF-β1 was quantified using commercially pure TGF-β1 as a standard and was determined to represent less than 1% of the BP protein. The antibody analysis indicated that each of the proteins listed in FIG. 14 is present in BP.

Figure 5:
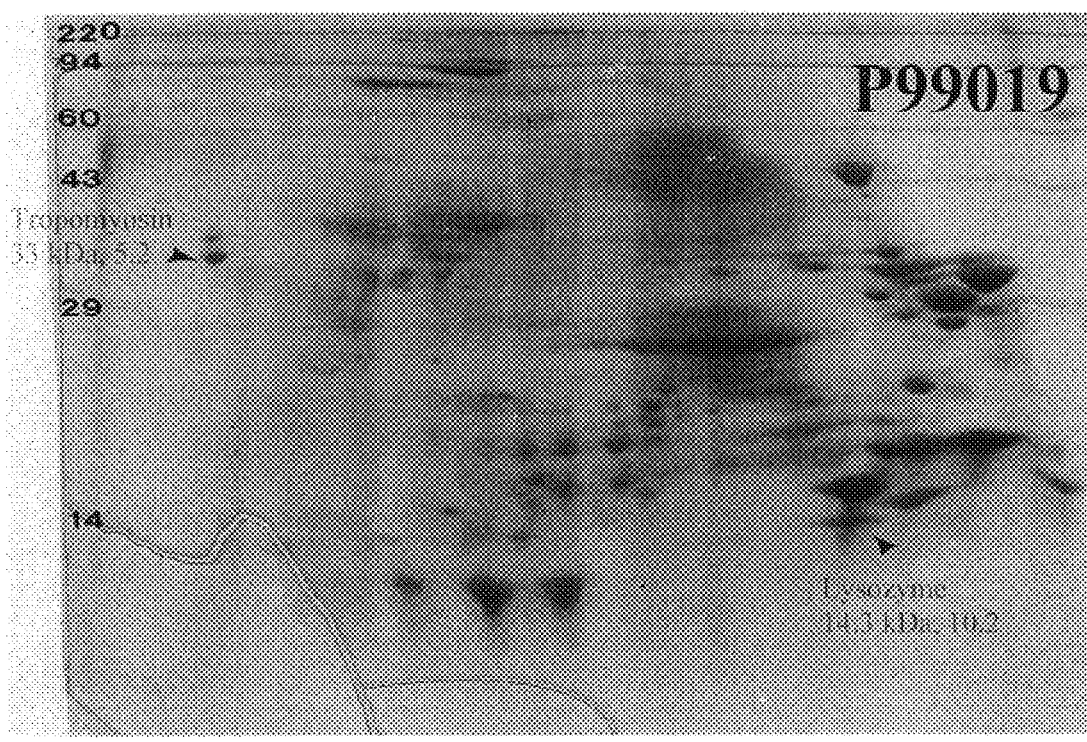
FIG. 5 is a two dimensional (2-D) SDS-PAGE gel of a protein mixture according to an embodiment of the present invention with internal standards indicated by arrows.
Figure 6:
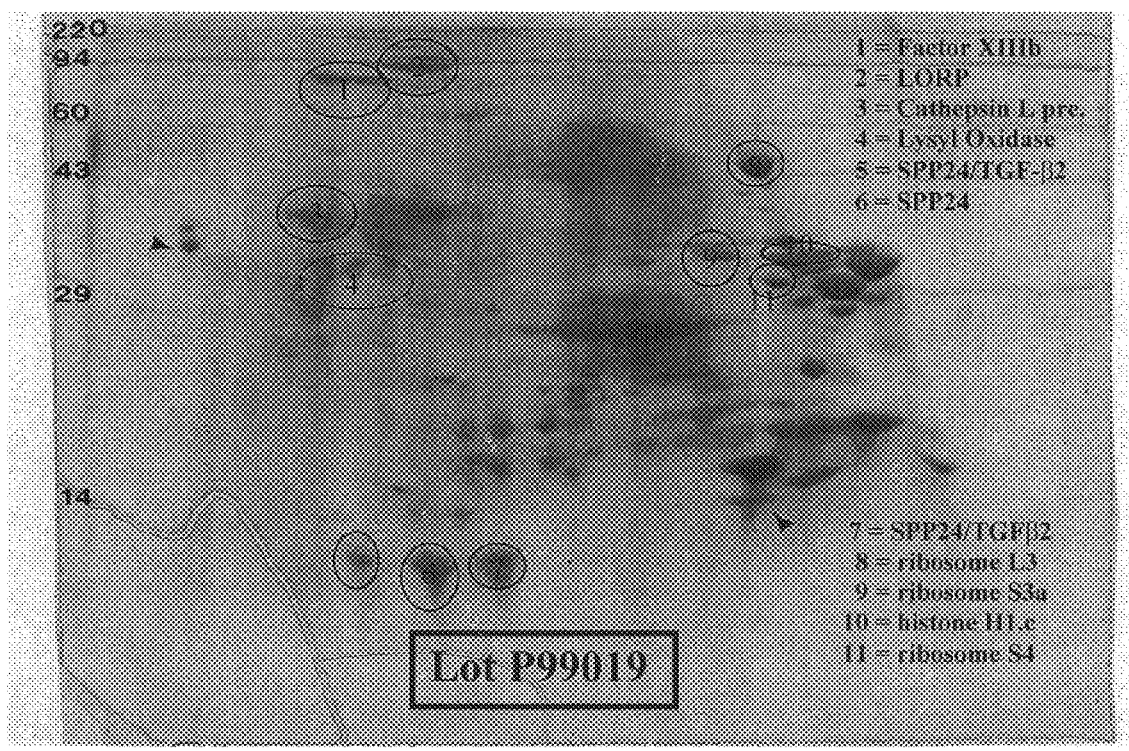
FIG. 6 is a 2-D SDS-PAGE gel of a protein mixture according to an embodiment of the present invention with circled proteins identified as in the legend.

The BP was further characterized by 2-D gel electrophoresis, as shown in FIGS. 5–6. The proteins are separated in horizontal direction according to charge (pI) and in the vertical direction by size as described in two-dimensional electrophoresis adapted for resolution of basic proteins was performed according to the method of O'Farrell et al. (O'Farrell, P. Z., Goodman, H. M. and O'Farrell, P. H., Cell, 12: 1133–1142, 1977) by the Kendrick Laboratory (Madison, Wis.). Two-dimensional gel electrophoresis techniques are known to those of skill in the art. Non-equilibrium pH gradient electrophoresis ("NEPHGE") using 1.5% pH 3.5–10, and 0.25% pH 9–11 ampholines (Amersham Pharmacia Biotech, Piscataway, N.J.) was carried out at 200 V for 12 hrs. Purified tropomyosin (lower spot, 33,000 KDa, pI 5.2), and purified lysozyme (14,000 KDa, pI 10.5–11) (Merck Index) were added to the samples as internal pI markers and are marked with arrows.

After equilibration for 10 min in buffer "0" (10% glycerol, 50 mM dithiothreitol, 2.3% SDS and 0.0625 M tris, pH 6.8) the tube gel was sealed to the top of a stacking gel which is on top of a 12.5% acrylamide slab gel (0.75 mm thick). SDS slab gel electrophoresis was carried out for about 4 hrs at 12.5 mA/gel.

After slab gel electrophoresis two of the gels were coomassie blue stained and the other two were transferred to transfer buffer (12.5 mM Tris, pH 8.8, 86 mM Glycine, 10% MeoH) transblotted onto PVDF paper overnight at 200 mA and approximately 100 volts/two gels. The following proteins (Sigma Chemical Co., St. Louis, Mo.) were added as molecular weight standards to the agarose which sealed the tube gel to the slab gel: myosin (220,000 KDa), phosphorylase A (94,000 KDa), catalase (60,000 KDa), actin (43,000 KDa), carbonic anhydrase (29,000 KDa) and lysozyme (14,000 KDa). FIG. 5 shows the stained 2-D gel with size standards indicated on the left. Tropomyosin (left arrow) and lysozyme (right arrow) are also indicated.

The same gel is shown in FIG. 6 with several identified proteins indicated by numbered circles. The proteins were identified by mass spectrometry and amino acid sequencing of tryptic peptides, as described above. The identity of each of the labeled circles is provided in the legend of FIG. 6.

Figure 8:
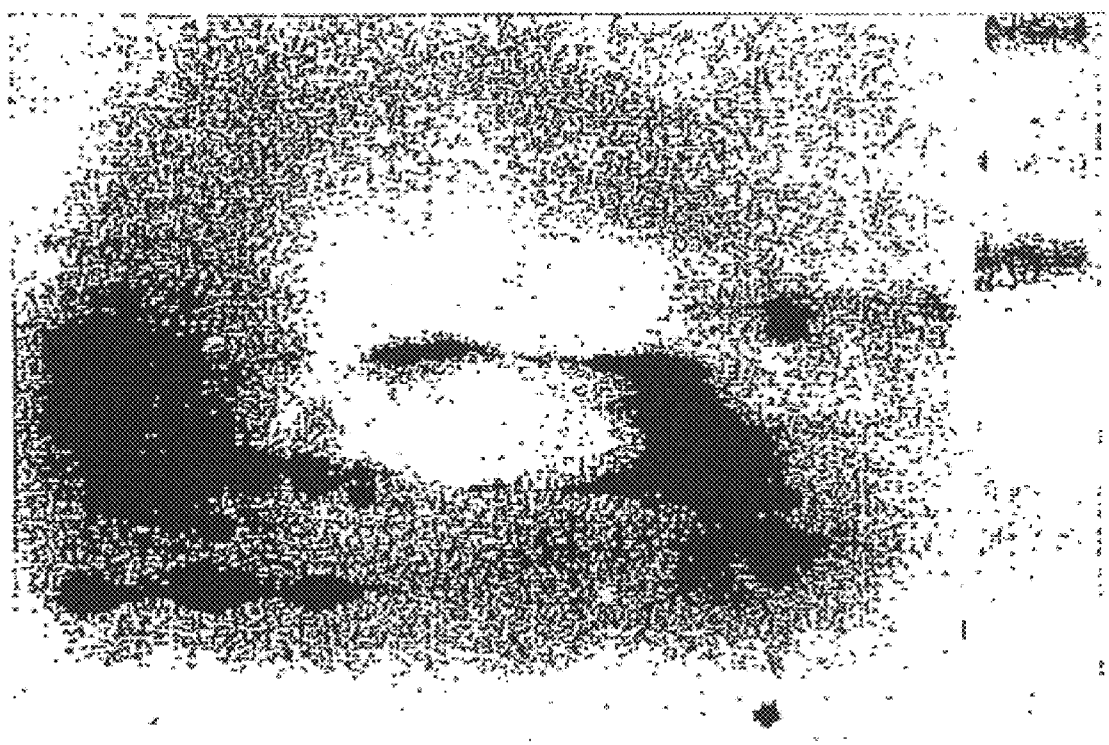
FIG. 8 is a 2-D gel Western blot of a protein mixture according to an embodiment of the present invention labeled with anti-phosphotyrosine antibody.

Because several of the proteins migrated at more than one size (e.g., BMP-3 migrating as 6 bands) investigations were undertaken to investigate the extent of post-translation modification of the BP components. Phosphorylation was measured by anti-phosphotyrosine immunoblot and by phosphatase studies. FIG. 8 shows a 2-D gel, electroblotted onto filter paper and probed with a phosphotyrosine mouse monoclonal antibody by SIGMA (# A-5964). Several proteins were thus shown to be phosphorylated at one or more tyrosine residues.

Figure 9A:
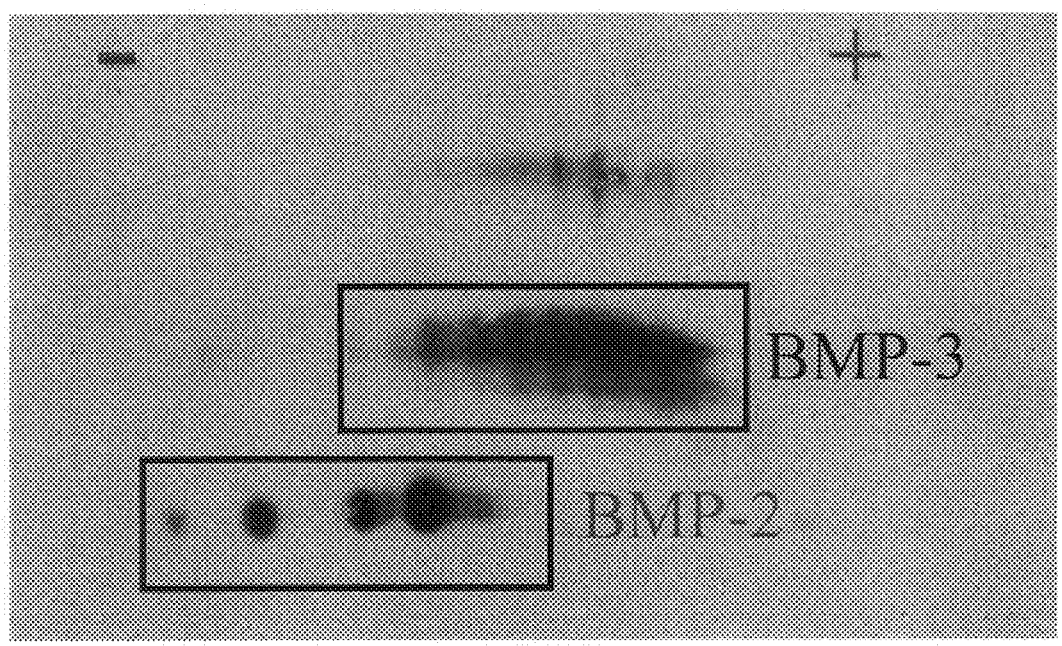
FIGS. 9A–D are 2-D gel Western blots of a protein mixture according to an embodiment of the present invention, labeled with indicated antibodies.
Figure 9B:
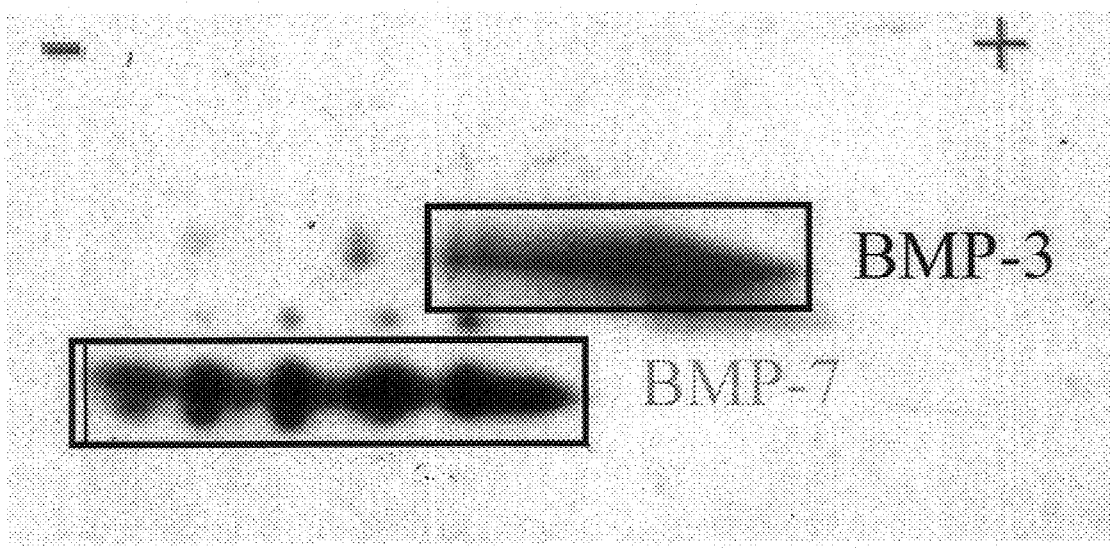
Figure 9C:
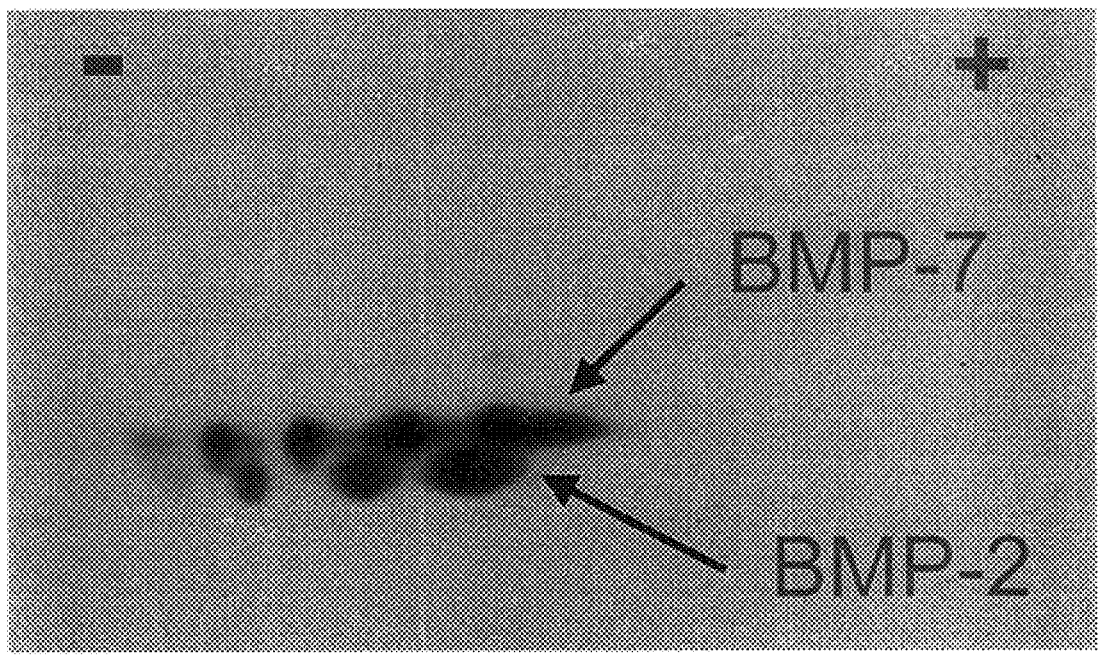
Figure 9D:
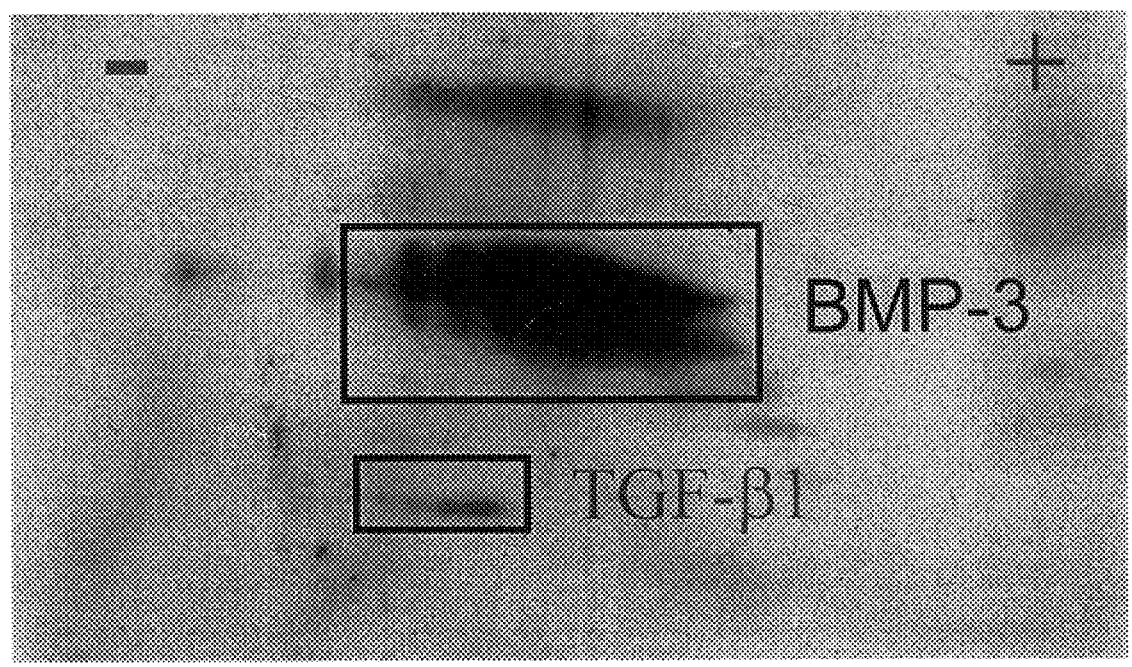

Similar 2-D electroblots were probed with BP component specific antibodies, as shown in FIGS. 9A–D. The filters were probed with BMP-2, BMP-3 (FIG. 9A), BMP-3, BMP-7 (FIG. 9B), BMP-7, BMP-2 (FIG. 9C), and BMP-3 and TGF-β1 (FIG. 9D). Each shows the characteristic, single-size band migrating at varying pI, as is typical of a protein existing in various phosphorylation states.

For the phosphatase studies, BP in 10 mM HCl was incubated overnight at 37° C. with 0.4 units of acid phosphatase (AcP). Treated and untreated samples were added to lyophilized discs of type I collagen and evaluated side by side in the subcutaneous implant rat bioassay, as previously described in U.S. Pat. Nos. 5,290,763, 5,563,124 and 5,371, 191. Briefly, 10 (g of BP in solution was added to lyophilized collagen discs and the discs implanted subcutaneously in the chest of a rat. The discs were then recovered from the rat at 2 weeks for the alkaline phosphotase ("ALP"—a marker for bone and cartilage producing cells) assay or at 3 weeks for histological analysis. For ALP analysis of the samples, the explants were homogenized and levels of ALP activity measured using a commercial kit. For histology, thin sections of the explant were cut with a microtome, and the sections stained and analyzed for bone and cartilage formation.

Both native- and phosphatase-treated BP samples were assayed for morphogenic activity by mass of the subcutaneous implant (explant mass) and ALP score. The results showed that AcP treatment reduced the explant mass and ALP score from 100% to about 60%. Thus, phosphorylation is important for BP activity.

The BP was also analyzed for glycosylation. FIG. 10 shows an SDS-PAGE gel stained with periodic acid schiff (PAS)—a non-specific carbohydrate stain, indicating that several of the BP components are glycosylated (starred protein identified as BMP-3 ). FIGS. 11–12 show immunodetection of two specific proteins (BMP-7, FIG. 14 and BMP-2, FIG. 15) treated with increasing levels of PNGase F (Peptide-N-Glycosidase F). Both BMP-2 and BMP-7 show some degree of glycoslyation in BP, but appear to have some level of protein resistant to PNGase F as well (plus signs indicate increasing levels of enzyme). Functional activity of PNGase F and sialadase treated samples were assayed by explant mass and by ALP score, as shown in FIGS. 13A and 13B, which shows that glycosylation is required for full activity.

In summary, BMPs 2, 3 and 7 are modified by phosphorylation and glycosylation. These post-translation modifications affect protein morphogenic activity, 33% and 50% respectively, and care must be taken in preparing BP not to degrade these functional derivatives.

Growth factor mixtures prepared according to the foregoing patents and patent applications have been shown to provide an angiogenic response when implanted in heart muscle tissue, as described in U.S. patent application Ser. No. 09/748,038, filed Dec. 22, 2000 and entitled "Method of Promoting Natural Bypass," which is incorporated by reference herein.

In addition, such growth factor mixtures are known to provide an osteogenic response when incorporated into or adjacent to bone tissue, and to promote wound healing and fibrous tissue regeneration. Accordingly, without being restricted to a particular theory, it is believed that the present invention functions by provided a localized healing response based upon local cell recruitment and proliferation, which may provide suitable annular tissue regeneration in the human heart.

The growth factor mixture may be coupled to the nonresorbable annuloplasty ring by a number of techniques known in the art. In a preferred embodiment, the growth factor mixture is dissolved in 10 mM HCl, or another suitable dilute acid solution, to provide a growth factor solution. The growth factor may be incorporated into the annuloplasty ring at concentrations ranging from 1 nanogram to 1 milligram, preferably from 0.1 micrograms to 100 micrograms. Once the desired concentration of the growth factor mixture is established, the growth factor solution is then delivered to the annuloplasty ring by dipping the ring into the solution, or, more preferably, a desired amount of the solution is applied by dripping the desired amount of the growth factor solution onto a cloth covered ring. The acid solution is then allowed to evaporate, leaving the growth factors deposited on the ring, within the pores or mesh of the external cloth, for instance. Alternatively, another suitable delivery means such as spraying may be used to impregnate the ring with the desired amount of growth factor mixture.

In another embodiment, an annuloplasty ring according to the present invention comprises an interior polymeric core and a polymer foam filler material, covered by an exterior cloth covering suitable for allowing the surgeon to suture the ring to the valve annulus during surgery. The growth factor mixture may be added to any or all of the polymer core, foam filler, and cloth covering, or any other porous or permeable ring component that will permit the associated growth factors to disassociate or come into contact with the tissue at the surgical site. By employing a ring having a foam filler, for instance, the growth factor solution may be injected into the ring with a syringe.

Another alternative way of making an annuloplasty ring with tissue growth inducing properties involves compounding the growth factor mixture in a resorbable polymer to obtain a polymeric growth factor reservoir to facilitate delivery of the growth factor mixture over a relatively long period of time, i.e. from a week or less to several months or longer. Existing resorbable polymers such as polyglycolic acid (PGA), polylactic acid (PLA), or other known resorbable suture materials, and mixtures and derivatives thereof, may be suitable for this purpose. The growth-factor loaded polymeric growth factor reservoir is disposed inside the outer covering of an annuloplasty ring. In this embodiment, although the cloth covering and, in preferred embodiments, an additional polymeric core are non-resorbable, the polymeric growth factor reservoir can degrade over time. In a preferred embodiment, both the outer surface impregnation and the polymeric growth factor reservoir are incorporated into the annuloplasty ring. In this alternative, the surface impregnation may be used to deliver rapidly a relatively high dose of the growth factor mixture, while the resorbable polymeric growth factor reservoir delivers a lower dose of the growth factor mixture over a longer time. As described above, a preferred way of loading the growth factor mixture is to impregnate a cloth surface so as to rapidly initiate a healing response. The growth factor mixture may be delivered to the adjacent tissue simply by diffusion from the pores of the cloth exterior or foam filler material after the HCl solvent is evaporated off. Alternatively, both extended delivery via a resorbable polymer, and rapid delivery via diffusion, may be used.

Studies have shown that the growth of tissue into the suturable fabric of annuloplasty rings can attract circulating bacteria or other pathogens which can colonize in the surgical wound surrounding the implant. Accordingly, in addition to the growth factor mixture, other therapeutic agents, such as antibiotics may be added to the annuloplasty ring for rapid and/or gradual release to the adjacent tissue according to methods known in the art. In a particularly preferred embodiment, the antibiotics comprise rifampin and minocycline, which may be incorporated into the annuloplasty ring by dissolving the antibiotics into a suitable solvent such as methanol to obtain an antibiotic solution which is then applied to the annuloplasty ring by dipping, spraying or other known techniques.

By providing a non-resorable annuloplasty ring comprising a growth factor mixture, and, optionally, other therapeutic agents, a prosthetic device having all the advantages of existing non-resorbable annuloplasty rings, plus an added tissue healing response, may be achieved. While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow. The disclosures of all patents, patent applications and publications cited herein are incorporated by reference in their entirety.

What is claimed is:

1. An annuloplasty prosthesis comprising:
a non-resorbable ring and
a growth factor associated with said ring for inducing growth of heart valve annulus tissue, said growth factor comprising at least one bone morphogenetic protein selected from the group consisting of: BMP-2, BMP-3, BMP-4, BMP-5, BMP-6, and BMP-7.

2. The prosthesis of claim 1 wherein said growth factor comprises BMP-2.

3. The prosthesis of claim 1 wherein said growth factor comprises BMP-3, BMP-2, BMP-4, BMP-5, BMP-6, and BMP-7.

4. The prosthesis of claim 1 wherein said growth factor comprises a bone morphogenetic protein selected from the group consisting of: BMP-2, BMP-7, and mixtures of BMP-2 and BMP-7.

5. The prosthesis of claim 1 wherein said ring comprises a foam filler material.

6. The prosthesis of claim 1 further comprising at least one antibiotic selected from the group consisting of minocycline and rifampin.

7. The prosthesis of claim 1 wherein said ring comprises at least one flexible portion.

8. The prosthesis of claim 1 wherein said ring comprises at least one rigid portion.

9. The prosthesis of claim 1 wherein said ring comprises at least one semi-rigid portion.

10. A method of treating a patient having a diseased or defective heart valve, the method comprising:

surgically implanting an annuloplasty prosthesis comprising a non-resorbable ring and a growth factor associated with said ring, said growth factor comprising at least one bone morphogenetic protein selected from the group consisting of: BMP-2, BMP-3, BMP-4, BMP-5, BMP-6, and BMP-7 in the annulus of said diseased or defective heart valve; and rapidly delivering said growth factor to tissue adjacent said annulus.

11. The method of claim 10 further comprising gradually delivering said growth factor to tissue adjacent said annulus.

12. The method of claim 10 wherein said prosthesis further comprises a porous foam filler material and said method further comprises diffusing said growth factor from the pores of said foam.

13. The method of claim 10 wherein said prosthesis further comprises a porous foam filler material and a porous cloth exterior and said method further comprises both rapidly and gradually delivering said growth factor adjacent said annulus.

* * * * *